United States Patent
Johnson et al.

(10) Patent No.: US 8,844,139 B2
(45) Date of Patent: Sep. 30, 2014

(54) METHODS OF MAKING MULTILAYER ANATOMICAL ALL-CERAMIC DENTAL APPLIANCES

(75) Inventors: Ryan E. Johnson, Peoria, IL (US); Naimul Karim, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/995,553

(22) PCT Filed: Dec. 20, 2011

(86) PCT No.: PCT/US2011/065961
§ 371 (c)(1),
(2), (4) Date: Jun. 19, 2013

(87) PCT Pub. No.: WO2012/087999
PCT Pub. Date: Jun. 28, 2012

(65) Prior Publication Data
US 2013/0277874 A1    Oct. 24, 2013

Related U.S. Application Data

(60) Provisional application No. 61/425,799, filed on Dec. 22, 2010.

(51) Int. Cl.
*A61C 13/00* (2006.01)
*A61C 13/003* (2006.01)
*A61C 13/20* (2006.01)

(52) U.S. Cl.
CPC ......... *A61C 13/0006* (2013.01); *A61C 13/0004* (2013.01); *A61C 13/0022* (2013.01)
USPC ....................... 29/896.1; 29/896.11

(58) Field of Classification Search
CPC ............... A61C 13/00; A61C 13/0003; A61C 13/0004; A61C 13/0006; A61C 13/130019; A61C 13/0013; A61C 13/08
USPC ......... 29/896.1, 896.11; 264/16, 19; 700/118, 700/119
See application file for complete search history.

(56) References Cited

U.S. PATENT DOCUMENTS

| 5,622,551 A | 4/1997 | Erbe |
| 6,482,284 B1 | 11/2002 | Reidt |

(Continued)

FOREIGN PATENT DOCUMENTS

| EP | 2184030 | 5/2010 |
| WO | 01/35854 | 5/2001 |

(Continued)

OTHER PUBLICATIONS

International Search Report PCT/US2011/065961; Apr. 20, 2012; 3 pgs.
Beuer et al., "High-strength CAD/CAM-fabricated veneering material sintered to zirconia copings—A new fabrication mode for all-ceramic restorations", Dental Materials 25 (2009) 121-128.

(Continued)

*Primary Examiner* — Alexander P Taousakis
(74) *Attorney, Agent, or Firm* — Nicole J. Einerson

(57) ABSTRACT

A method of making a multilayer all-ceramic dental appliance. A first article can be formed of a first material based on a first digital surface representation having a desired outer shape of the dental appliance. A portion of the first article can be removed to form an outer layer comprising a cavity dimensioned to accommodate an inner layer. A second article can be formed by filling the cavity of the first article with a second material. The second article can be further processed, as desired. For example, a desired inner shape can be formed in the second article. Such a desired inner shape can be based on a second digital surface representation of a dental object configured to receive the dental appliance. At least one of the first article, the outer layer, and the second article can be fired, for example, while still being coupled to a support.

20 Claims, 3 Drawing Sheets

(56) References Cited

U.S. PATENT DOCUMENTS

| | | | |
|---|---|---|---|
| 6,669,875 B2 | 12/2003 | Meyertholen | |
| 7,563,397 B2* | 7/2009 | Schulman et al. | 264/16 |
| 7,605,817 B2 | 10/2009 | Zhang | |
| 7,698,014 B2* | 4/2010 | Dunne et al. | 700/118 |
| 2004/0155975 A1 | 8/2004 | Hart | |
| 2005/0276672 A1 | 12/2005 | Prince | |
| 2010/0058588 A1 | 3/2010 | Heinz | |
| 2010/0219546 A1* | 9/2010 | Puttler et al. | 264/16 |
| 2012/0175800 A1* | 7/2012 | Ruppert et al. | 264/17 |
| 2012/0251979 A1* | 10/2012 | Karim et al. | 433/201.1 |
| 2012/0277899 A1* | 11/2012 | Chun et al. | 700/118 |
| 2013/0056892 A1* | 3/2013 | Johnson et al. | 264/19 |
| 2013/0081272 A1* | 4/2013 | Johnson et al. | 29/896.1 |
| 2014/0147225 A1* | 5/2014 | Cornell et al. | 409/225 |

FOREIGN PATENT DOCUMENTS

| | | |
|---|---|---|
| WO | 2009/070469 | 6/2009 |
| WO | 2011/106132 | 9/2011 |
| WO | 2011/159503 | 12/2011 |
| WO | 2011/159520 | 12/2011 |
| WO | 2012/087997 | 6/2012 |

OTHER PUBLICATIONS

"Porcelain Veneer Materials", About Porcelain Veneers© 2101—[online-printed Nov. 8, 2010], 3 pages. <www.aboutporcelainveneers.com/index.cfm/PV-Materials.cfm>.

"Glass Ceramic Block for Cerec® and inLab", Technical Product Profile—Paradigm C; 3M ESPE (03.06); 32 pgs.

* cited by examiner

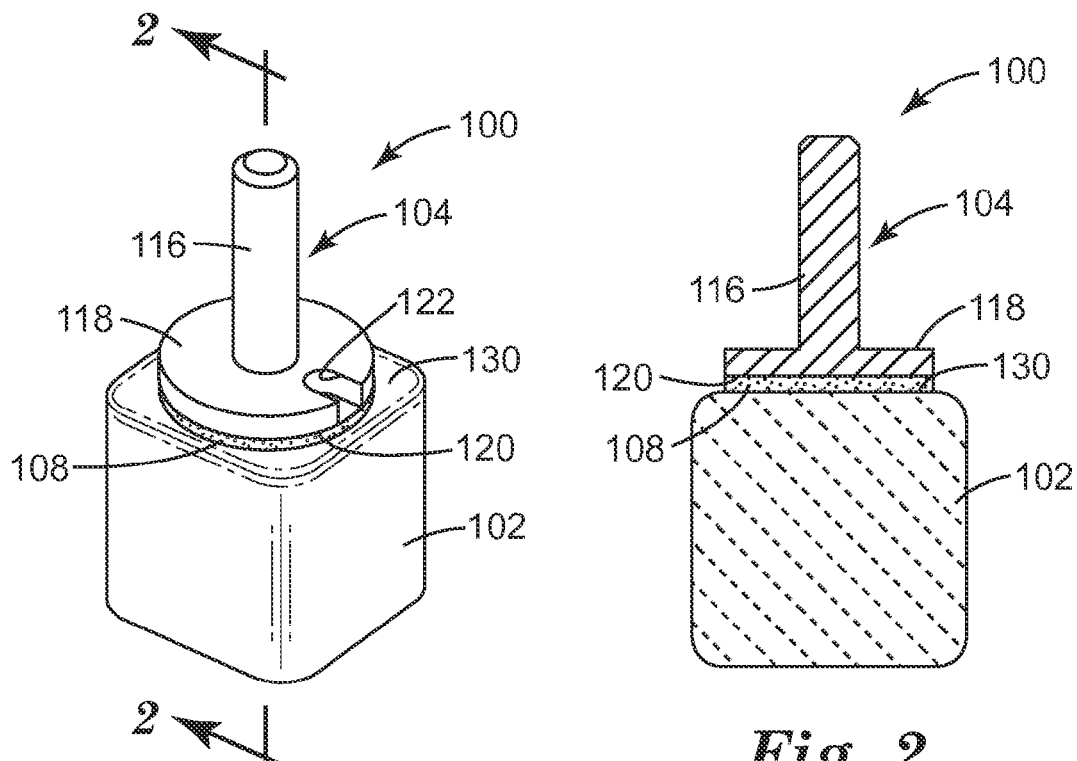
Fig. 1
Fig. 2
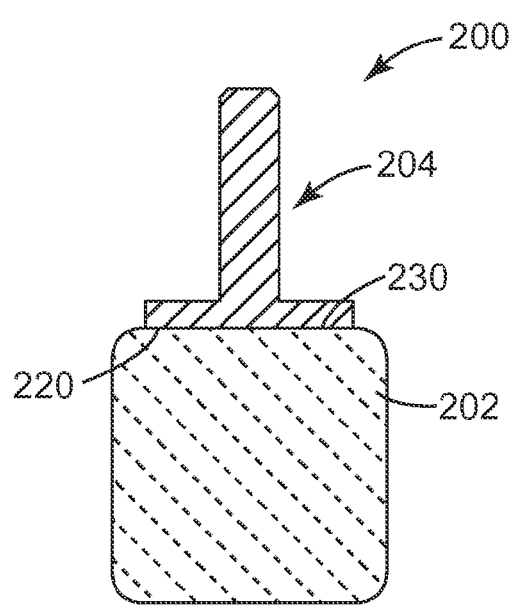
Fig. 3

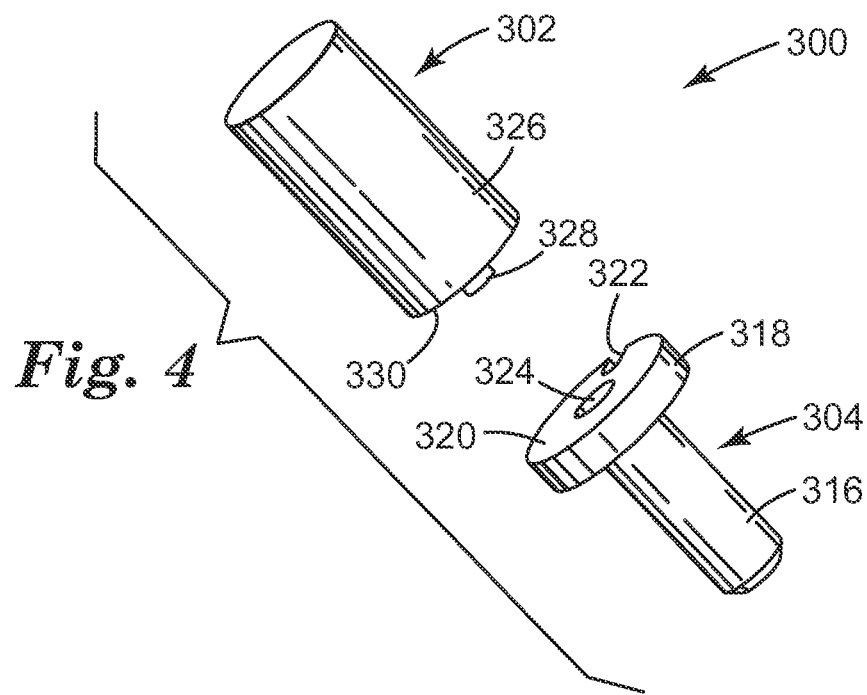
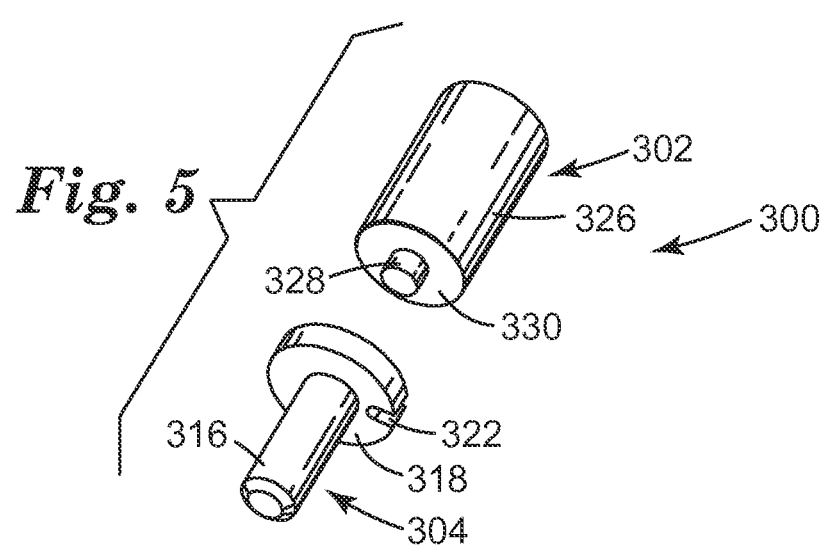

METHODS OF MAKING MULTILAYER ANATOMICAL ALL-CERAMIC DENTAL APPLIANCES

FIELD

The present disclosure is generally related to methods and workflows of making layered dental appliances, such as temporary or permanent dental restorations; particularly, to digital workflows for making multilayer, anatomical, all-ceramic dental appliances; and more particularly, to at least partially chairside digital workflows for multilayer, anatomical, all-ceramic dental appliances.

BACKGROUND

Digital dentistry generally includes using or creating one or more digital data files to prepare a dental appliance having a desired outer and/or inner shape and dimension. In some existing workflows, a desired outer shape of a final dental appliance can be determined; a tooth can be prepared (e.g., ground to a tooth stump); and a desired inner shape of the final dental appliance can be determined from the prepared tooth. A data file comprising the desired outer shape and the desired inner shape can then be used to create the final dental appliance having a desired outer and inner shape. For example, in some existing systems, the dental appliance can be formed by milling. However, milled dental appliances generally have a monolithic visual appearance, and uniform structural properties throughout, due to the corresponding, monolithic composition of dental mill blanks.

SUMMARY

The present disclosure generally relates to workflows that allow a desired outer shape (i.e., external surface, contours, etc.) of a dental appliance to be determined and created separately from that of a desired inner shape (i.e., internal surface, contours, etc., e.g., for accommodating a prepared tooth, an implant, an implant abutment, a healing cap, or the like, or combinations thereof) of the same dental appliance; thus, generally separating the step for preparing the desired outer shape from the step for preparing the desired inner shape of a dental appliance.

Furthermore, the present disclosure generally relates to workflows that allow a desired outer layer of a dental appliance to be determined and created separately from that of a desired inner layer of the same dental appliance. The outer layer of the dental appliance can include a desired outer shape, as well as a desired inner shape or cavity. The inner layer of the dental appliance can also include a desired outer shape (e.g., that can match the inner shape of the outer layer, or that can be sized to accommodate an adhesive or bonding layer between the layers), and a desired inner shape (e.g., for accommodating a prepared tooth, an implant, an implant abutment, healing cap, or the like, or combinations thereof). For example, the inner layer can include a dental core or framework of a dental restoration. As a result, methods of the present disclosure can include separation of (e.g., temporally and/or spatially) the steps for designing and creating an outer layer of a dental appliance from steps for designing and creating an inner layer of the same dental appliance.

Some embodiments of the present disclosure provide a method of making a dental appliance. The method can include providing a first digital surface representation of a desired outer shape of a dental appliance; forming a first article of a first material having the desired outer shape based on the first digital surface representation, the first material comprising at least one of a glass, a glass-ceramic, a porcelain, and a ceramic; removing an inner portion of the first article to form an outer layer of the dental appliance comprising a cavity dimensioned to accommodate an inner layer; forming a second article by filling the cavity of the first article with a second material adapted to form the inner layer, the second material comprising at least one of a glass, a glass-ceramic, a porcelain, and a ceramic; and firing at least one of the first article, the outer layer, and the second article.

Some embodiments of the present disclosure provide a method of making a multilayer all-ceramic dental appliance. The method can include providing a first digital surface representation of a desired outer shape of a dental appliance; providing a dental blank assembly comprising a blank coupled to a support, the blank being formed of a first material, the first material comprising at least one of a glass, a glass-ceramic, a porcelain, and a ceramic; forming a first article of the blank while the blank is coupled to the support, the first article having the desired outer shape based on the first digital surface representation; providing a first assembly comprising the first article coupled to the support; removing an inner portion of the first article, while the first article is coupled to the support, to form an outer layer of the dental appliance comprising a cavity dimensioned to accommodate an inner layer; providing a second assembly comprising the outer layer coupled to the support; forming a second article by filling the cavity of the outer layer with a second material adapted to form the inner layer, the second material comprising at least one of a glass, a glass-ceramic, a porcelain, and a ceramic; providing a third assembly comprising the second article coupled to the support; and firing at least one of the first assembly, the second assembly, and the third assembly.

Other features and aspects of the present disclosure will become apparent by consideration of the detailed description and accompanying drawings.

BRIEF DESCRIPTION OF THE DRAWINGS

FIG. 1 is a perspective view of a dental blank assembly according to one embodiment of the present disclosure.

FIG. 2 is a cross-sectional side view of the dental blank assembly of FIG. 1, taken along line 2-2 of FIG. 1.

FIG. 3 is a side cross-sectional view of a dental blank assembly according to another embodiment of the present disclosure.

FIG. 4 is an exploded perspective view of a dental blank assembly according to another embodiment of the present disclosure.

FIG. 5 is an exploded perspective view of the dental blank assembly of FIG. 4, shown in a different orientation.

DETAILED DESCRIPTION

Figure 6:
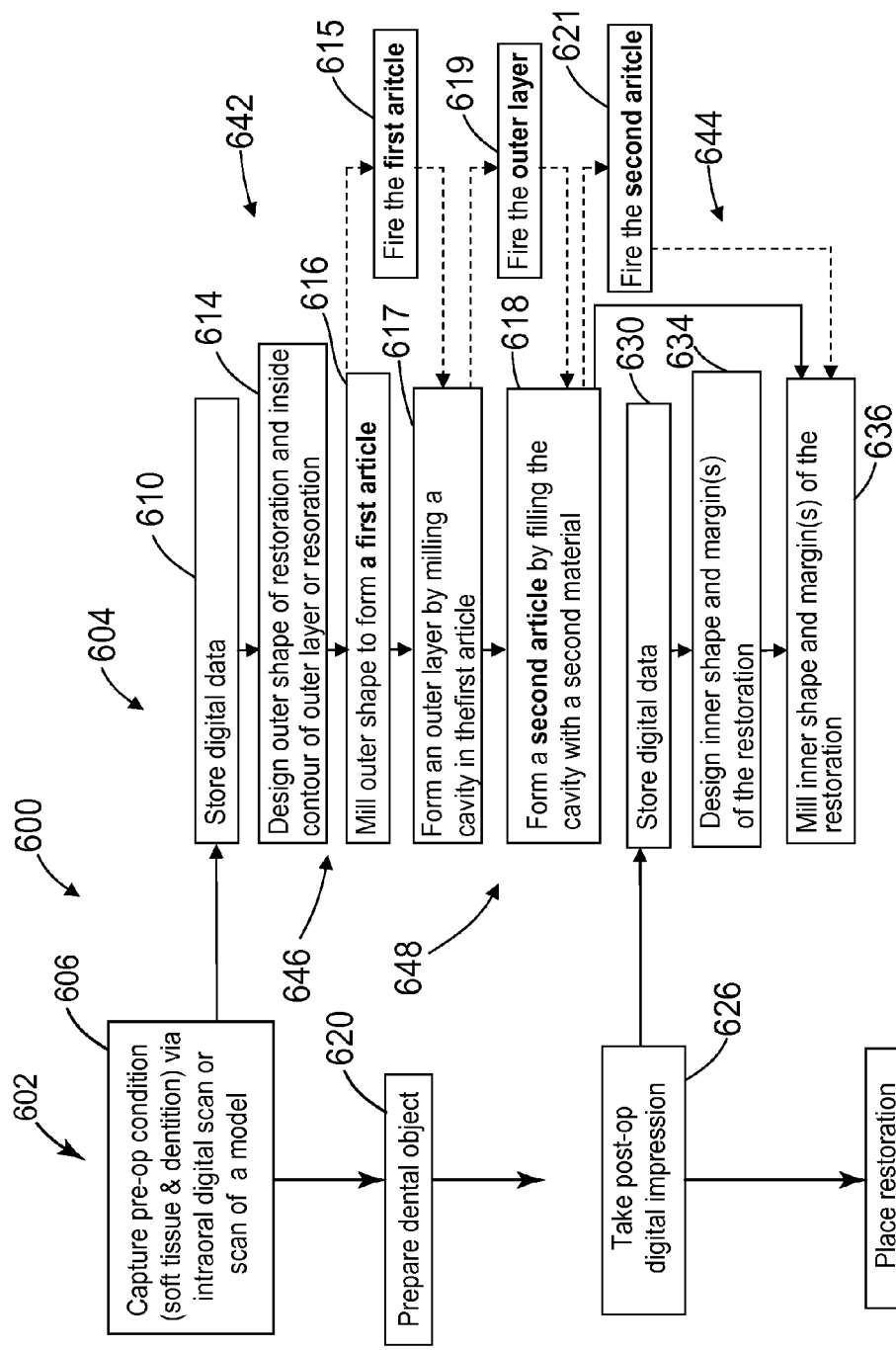
FIG. 6 illustrates a flowchart of a method of making a layered, anatomical, all-ceramic dental appliance, according to one embodiment of the present disclosure.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having"

and variations thereof herein is meant to encompass the items listed thereafter and equivalents thereof as well as additional items. Unless specified or limited otherwise, the terms "affixed," and "coupled" and variations thereof are used broadly and encompass both direct and indirect affixations and couplings. Further, "coupled" is not restricted to physical or mechanical connections or couplings. It is to be understood that other embodiments may be utilized, and structural or logical changes may be made without departing from the scope of the present disclosure. Furthermore, terms such as "front," "rear," "top," "bottom," "upper," "lower," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to workflows that can be used to create layered, anatomical, all-ceramic dental appliances. In some embodiments, the dental appliances can also be multi-chromatic and/or biomimetic. In addition, the workflows of the present disclosure can allow for a desired outer shape of the dental appliance (or of each layer of the dental appliance) to be created separately from creation of a desired inner shape of the dental appliance (or of each layer of the dental appliance). The desired outer shape of the dental appliance is generally sized and shaped to accommodate a patient's mouth, or a portion of the patient's mouth in which the dental appliance will be placed. The desired inner shape of the dental appliance, however, is generally sized and shaped to fit over a dental object, such as a prepared tooth stump, an implant, an implant abutment, healing cap, or the like, or combinations thereof.

The desired outer shape can be provided by an outer layer of the dental appliance, while the desired inner shape can be provided by an inner layer of the dental appliance. The present disclosure also generally relates to methods and workflows for making dental appliances that do not require the outer layer and the inner layer of a dental appliance both be designed and known prior to creating the outer layer. By not requiring that both the outer layer and the inner layer be known prior to any forming (e.g., machining) steps, forming a desired outer layer of the dental appliance can be performed separately from forming a desired inner layer.

The outer layer and the inner layer, and any other layers, described herein that are formed by methods of the present disclosure generally include major or significant portions of the resulting dental appliance, and generally do not include bonding materials or bonding layers, such as adhesives or bonding layers used, for example, to couple the dental appliance to a dental object (e.g., a tooth stump) and/or to couple layers of the dental appliance together. For example, in some embodiments, the outer layer, the inner layer, and any other layers described herein as forming a portion the dental appliance, generally form at least about 80% by volume (vol %) of the dental appliance, in some embodiments, at least about 90% by volume, and in some embodiments, at least about 95% by volume. Bonding materials used to couple together layers of the dental appliance and/or to couple the dental appliance to a dental object, if employed, generally do not significantly contribute to the overall optical properties of the dental appliance.

As used herein the term "anatomical" generally refers to an object (e.g., a dental appliance) that is designed to closely match the appearance and organization of a natural tooth. That is, an "anatomical" dental appliance generally includes an appliance that closely mimics the appearance of a natural tooth, including the positioning of internal tooth structures (e.g., mammelons), the positioning and structure of outer shapes and surfaces, the relative positioning of such internal and external structures, and the distribution of shades and colors throughout the dental appliance. For example, in some embodiments, the dental appliance can be layered and can include an outer layer having a desired outer and inner shape or contour and a desired shade or color, as well as an inner layer having a desired outer and inner shape or contour and a desired shade or color, where the inner layer is also positioned relative to the outer layer in a desired orientation. Contrary to an anatomical dental appliance might be an appliance that is formed from a single material (e.g., from a single blank), or even from a multilayer blank, or a blank comprising more than one material or shade. In such cases, the layers of the mill blank most likely will not match up with the desired anatomical shape of each layer of a desired dental appliance, and certainly not as well as a multilayer dental appliance in which each layer is formed separately to mimic the appearance and structure of a natural tooth.

As a result, dental appliances formed according to methods of the present disclosure can also be multi-chromatic and can be more natural-looking and/or aesthetically-pleasing. As used herein, the term "multi-chromatic" generally refers to an object (e.g., a dental appliance) that includes two or more layers, and wherein each layer is different from another layer with respect to at least one optical property. Such optical properties can include, but are not limited to, color or shade, transparency/translucency/opacity, reflectance, gloss or shine, refractive index, other suitable optical properties, or combinations thereof. Such optical properties can typically be visually distinguishable by the naked human eye. Methods and workflows for making multi-chromatic dental appliances are described in U.S. Application No. 61/355,876, filed Jun. 17, 2010, entitled, "Methods of Making Multi-chromatic Dental Appliances," which is incorporated herein by reference in its entirety.

As used herein, the term "biomimetic" generally refers to an object (e.g., a dental appliance) that is designed to imitate nature or biology in terms of visual aesthetics and/or function. Particularly, with respect to dental appliances, a "biomimetic" dental appliance can generally mimic the structural and/or material properties of a natural tooth, which generally has a harder enamel exterior and a softer dentin interior. For example, in some embodiments, the dental appliance can be layered and can preferably include a hard outer shell and a resilient internal structure, such that the internal structure can provide a sufficient amount of shock absorption that mimics a natural tooth. There may be situations in which a dental practitioner may choose to use a dental appliance that has a softer exterior and a harder interior. Therefore, in some embodiments, a biomimetic dental appliance can include two or more layers, and each layer can differ from another layer with respect to at least one structural and/or material property. Such structural and/or material (e.g., mechanical or physical) properties can include, but are not limited to, hardness, toughness, strength (e.g., strength under compression), impact resistance, elastic modulus, flexural modulus, abrasion resistance, polish retention, other suitable material properties, or combinations thereof. It can also be important in a biomimetic dental appliance that the outer layer and the inner layer (i.e., formed of a first material and a second material, respectively) have good interfacial bonding, for example, for structural integrity and sufficient biomimetics.

By providing an inner layer and an outer layer of different material properties, a more natural-functioning dental appliance can be formed. For example, in the case of dental restorations, such as crowns and bridges, an outer layer can include a certain level of hardness, stiffness, and/or strength (e.g., under compression) to mimic an outer enamel shell, while the inner layer can include a certain level of toughness and/or resilience to mimic an internal dentin layer. In the case of bridges, each tooth unit on the bridge can include an interior cavity that is milled (i.e., to form an outer layer) and filled to form an inner layer of a different material property than the outer layer.

In addition, the inner layer and outer layer can have different optical properties, which can provide a more natural-looking and aesthetically-pleasing dental appliance. For example, in the case of dental restorations, such as crowns and bridges, an outer layer can include a certain level of translucency and can be shaded to mimic an enamel layer, while the inner layer can also include a certain level of opacity and can be shaded to mimic a dentin layer (e.g., the inner layer can be slightly darker in color than the outer layer). In the case of bridges, each tooth unit on the bridge can include an interior cavity that is milled (i.e., to form an outer layer) and filled to form an inner layer of a different optical property (e.g., shade) than the outer layer.

In general, the dental appliances formed according to methods of the present disclosure are formed of ceramic-based materials, including, but not limited to, at least one of glasses, glass-ceramics, porcelains, ceramics, and combinations thereof. Definitions and examples of suitable materials are described below.

While the present disclosure may emphasize certain steps and certain types of dental articles, it will be understood that additional variations, adaptations, and combinations of the methods and systems below will be apparent to one of ordinary skill in the art. For example, there are a number of variants to computer-controlled milling that may be suitably employed. Similarly, a number of three-dimensional scanning technologies are available that might be suitably adapted to obtaining three-dimensional scans for the uses described herein. All such variations, adaptations, and combinations are intended to fall within the scope of this disclosure.

The methods of the present disclosure will generally be described as forming a two-layer dental appliance, including an outer layer and an inner layer. However, it should be understood that as many layers as necessary can be formed according to the techniques described herein, and the description of two layers is used only for simplicity and clarity. The phrases "outer layer" and "inner layer" can be used to describe an "outermost layer" and an "innermost layer," and as many intermediate layers as necessary can be formed between the outermost layer and the innermost layer, following the methods and workflows described herein.

The methods of the present disclosure can generally be facilitated with the use of a fireable dental blank assembly, such as that described in co-pending U.S. patent application Ser. No. 61/425,798, filed Dec. 22, 2010, which is incorporated herein by reference in its entirety. Such fireable dental blank assemblies can generally include a support and a blank (e.g., a mill blank) coupled to the support. The support can be used to provide support, proper positioning and/or registration of the blank for machining (e.g., in a dental mill) or handling, and particularly, for multi-step machining that may even occur in more than one tool or machine. A dental appliance (e.g., a dental restoration), or a portion thereof (e.g., an outer layer) can be formed from the blank. Such fireable dental blank assemblies can facilitate the methods of the present disclosure by allowing the blank to remain coupled to the support until the dental appliance is completed. For example, in some embodiments, the blank can remain coupled to the support throughout any firing steps that may occur during the processing of the blank. That is, in some embodiments, the support can be configured to withstand firing temperatures used to fire (e.g., densify) the blank at various stages in making a dental appliance. Examples of dental blank assemblies that can be used in the methods of the present disclosure are described in greater detail below, with reference to FIGS. 1-5.

The phrase "dental article" is to be understood as an article which can and is to be used in the dental or orthodontic area including dental laboratories, and can be used to describe even intermediates in a dental workflow process.

The phrase "dental appliance" generally refers to any dental or orthodontic appliance or restoration, dental mill blank, prosthetic device, or combination thereof. The appliance may be a finished appliance ready for introduction into the mouth of a patient, an appliance without the finishing (e.g. without stains) but with its final shape (i.e., a "net shape" appliance), or it may be a preformed or near-final dental appliance (i.e., a "near-net shape" appliance) subject to further processing before use, such as a dental mill blank.

The phrases "blank," "mill blank," "dental mill blank," "mill block," and "block" can be used interchangeably and generally refer to a solid block of material from which a desired product (e.g., a dental restoration) can be machined, and is not limited to the type of machining that will be used, even if referred to as a "mill" blank. A blank may have a size of about 10 mm to about 30 mm in two dimensions, for example may have a diameter in that range, and may be of a certain length in a third dimension. A blank for making a single crown may have a length of about 15 mm to about 30 mm, and a blank for making bridges may have a length of about 40 mm to about 80 mm. In some embodiments, a blank used for making a single crown can have a diameter of about 24 mm and a length of about 19 mm. In some embodiments, a blank used for making bridges can have a diameter of about 24 mm and a length of about 58 mm. In general, blanks are attached to a support, stub, or mandrel that fits into a milling machine.

The terms "support," "support section," "stub," "mandrel," "milling support," and "milling mandrel" can be used interchangeably and generally refer to a structure that can provide support, positioning, mounting, and/or registration of the blank during machining (e.g., in a dental mill) or handling. Supports can include rod-shaped, cylindrical, or "hat"-shaped structures, but can also be understood to include other structures, such as frames (e.g., a LAVA™ frame available from 3M ESPE, Seefeld, Germany).

The term "machining" generally refers to shaping a material by a machine, and can be employed to create custom-fit dental appliances having a desired shape and morphology. Machining can include, but is not limited to, one or more of milling, grinding, cutting, carving, abrading, polishing, controlled vaporization, electric discharge milling (EDM), cutting by water jet or laser, any other suitable method of cutting, removing, shaping or carving material, or a combination thereof. In some cases, milling can be faster and more cost-effective than grinding. The terms "blank," "mill blank," "dental mill blank," "mill block," and "block" can be used to describe a starting material that will be machined to form a dental appliance.

While machining a blank using a hand-held tool or instrument is possible, machining of the present disclosure particularly refers to machining by subtractive CAD/CAM processes, in which a digital workflow is used to determine the desired shape or features (e.g., in three dimensions), and/or to guide the machining process to remove material in order to form the desired shape. By way of example, in some embodiments, a specially designed tooth-shape (e.g., a positive of the tooth-shape and/or a negative of the tooth-shape) can be produced by a digital workflow. Such a digital workflow can include scanning a patient's mouth to develop a model for the desired dental appliance. Such scanning can be performed using an optical scanner that is coupled to a computer-aided design (CAD) system that functions in conjunction with a computer-integrated manufacturing (CIM) or computer-aided manufacturing (CAM) system. Such a CAD/CAM system is available, for example, under the trade designation LAVA™ from 3M ESPE AG (Seefeld, Germany).

Some embodiments of the present disclosure employ a CAD/CAM device capable of milling a blank, such as the Cerec System (available from Sirona Dental Systems, Germany) By using a CAD/CAM machining (e.g., milling) device, the dental appliance can be fabricated efficiently and with precision. During machining, the contact area may be dry, or it may be flushed with a lubricant. Alternatively, it may be flushed with an air or gas stream. Suitable lubricants can include water, oil, glycerin, ethylene glycols, silicones, or combinations thereof. After machining, some degree of finishing, polishing and adjustment may be necessary to obtain a custom fit and/or aesthetic appearance.

The phrase "dental restoration" is generally used to refer to any restoration that can be used in the dental field, including, but not limited to, crowns, partial crowns, inlays, onlays, abutments, bridges (e.g., including 2-unit, 3-unit, 4-unit, 5-unit or 6-unit bridges), implants, other suitable dental articles, and combinations thereof. The dental restoration can include a three-dimensional inner and outer surface including convex and concave structures. The thickness of a dental restoration can vary from very thin, for example at its edges and rims (e.g., less than about 0.1 mm) to considerably thick, for example, in the biting, or occlusal, area (e.g., up to about 7 mm). In some embodiments, the thickness of a dental restoration ranges from 0.3 mm to 0.5 mm.

The terms "ceramic" or "all-ceramic" are generally used to refer to materials that are considered to fall within the broad material class of "ceramic," and are formed of glass, glass-ceramic, porcelain, ceramic, or combinations thereof. For example, a "ceramic" or "all-ceramic" blank, support, dental blank assembly, or dental appliance would not include any structures formed of organic polymeric materials.

The term "glass" generally refers to a hard, brittle, transparent solid. Examples of glasses can include, but are not limited to, silica, borosilicate glass, sodium oxide, potassium oxide, calcium oxide, flint glass, soda-lime glass, other suitable glass components, or combinations thereof. A glass can include an inorganic product of fusion that has been cooled to a rigid condition without crystallizing. Some glasses contain silica as their main component and a certain amount of glass former.

The phrase "glass ceramic" generally refers to a material sharing many properties with both glass and more crystalline ceramics. It is formed as a glass, and then made to crystallize partly by heat treatment. The space between the crystallites is filled by the glassy matrix. Glass ceramics mainly refer to a mixture of alkali metal-, silicon-, and aluminium-oxides.

The term "porcelain" generally refers to a clay-based ceramic. Clay products are generally classified into two sub-classes—structural clay products and whitewares. Porcelain is an example of a whiteware in that porcelain becomes white and/or translucent after high-temperature firing. Porcelains are generally formed of clay (e.g., including alumina ($Al_2O_3$), silica ($SiO_2$), and other impurities) and other non-clay materials, such as flint, quartz, kaolin, and feldspar. Feldspars generally include aluminosilicate materials that contain $K^+$, $Na^+$, and $Ca^{2+}$ ions.

The term "ceramic" generally refers to an inorganic non-metallic material that can be produced by application of heat. Ceramics can be hard, porous and brittle and, in contrast to glasses or glass ceramics, can display an essentially purely crystalline structure.

The phrase "softening temperature" or "softening point" generally refers to the temperature, or range of temperatures, at which a material (e.g., in a solid phase) begins to slump under its own weight. For metals, in the present disclosure, the softening point is generally regarded as being the melting point of the metal or metal alloy. However, for materials that do not have a definite melting point, the softening point may be the temperature at which viscous flow of the material changes to plastic flow. For example, the softening point of a glass, a glass-ceramic, or a porcelain may occur at a glass-transition temperature of the material, and may be defined by a viscosity of 10 poise, in some embodiments, a viscosity of 10^4 poise, in some embodiments, a viscosity of 10^7.65 poise, and in some embodiments, a viscosity of 10^13 poise.

Any of the above materials—glasses, glass-ceramics, porcelains and ceramics—can shrink upon drying and/or firing, but a more detectable and/or significant amount of shrinkage may occur with ceramics, as compared to glasses, glass-ceramics, and porcelains.

"Pre-sintered" within the meaning of the present disclosure generally refers to a ceramic material (e.g., a pre-formed inner layer of a dental appliance) that has been treated with heat (e.g., a temperature ranging from about 900 to about 1100° C.) for about 1 to about 3 hours to such an extent that the raw breaking resistance (Weibull strength Sigma 0) of the dental ceramic appliance is within a range of about 15 to about 55 MPa or about 30 to about 50 MPa (measured according to the "punch on three ball test" (biaxial flexural strength) described in DIN EN ISO 6872, edition March 1999, with the following modifications: diameter of steel ball: 6 mm; diameter of support circle: 14 mm; diameter of flat punch: 3.6 mm; diameter of sample disc: 25 mm, thickness of sample disc: 2 mm; no grinding and polishing of samples.).

A pre-sintered ceramic material can include a porous structure and its density (e.g., which can be 3.0 $g/cm^3$ for an Yttrium stabilized $ZrO_2$ ceramic) can be less compared to a completely sintered or finally sintered (i.e., such that there will be no further sintering step) ceramic material (e.g., which can be 6.1 $g/cm^3$ for an Yttrium stabilized $ZrO_2$ ceramic). In some embodiments, the diameter of the pores can be in a range of about 50 nm to about 150 nm (corresponding to about 500 to about 1500 Å). In some embodiments, a pore diameter can be about 120 nm.

In some embodiments, pre-sintering of a glass and/or glass ceramic material can be effected in a temperature of at least about 500° C., and in some embodiments, at least about 600° C. In some embodiments, pre-sintering of a glass and/or glass ceramic material can be effected in a temperature of no greater than about 750° C., and in some embodiments, no greater than about 700° C. In some embodiments, pre-sintering of a glass and/or glass ceramic material can be effected in a temperature range of from about 500° C. to about 750° C., and in some embodiments, from about 600° C. to about 700° C.

The term "sintering" generally refers to making objects from a powder by heating the material (e.g., below its melting point—"solid state sintering") until its particles adhere to each other. Sintering can cause the densification of a porous material to a less porous material (or a material having less cells) having a higher density. In some cases, sintering can also include changes of the material phase composition (e.g., a partial conversion of an amorphous phase toward a crystalline phase).

The terms "sintering" and "firing" are used interchangeably herein. A pre-sintered ceramic framework can shrink during a sintering step, that is, if an adequate temperature is applied. The sintering temperature to be applied depends on the material chosen. For example, for $ZrO_2$-based ceramics, a sintering temperature (e.g., for sintering to full density) can range from about 1200° C. to about 1600° C. In some embodiments, $Al_2O_3$-based ceramics can be sintered at a temperature ranging from about 1300° C. to about 1700° C. However, if the dental blank assembly of the present disclosure will be fired as an assembly, the blank can be selected so as not to shrink to a point where it would detach from the support.

In some embodiments, in general, sintering of a glass and/or glass ceramic material to full density can be effected at a temperature of at least about 700° C., and in some embodiments, at least about 750° C. In some embodiments, sintering to full density of a glass and/or glass ceramic material can be effected at a temperature of no greater than about 1000° C., and in some embodiments, no greater than about 950° C. In some embodiments, sintering to full density of a glass and/or glass ceramic material can be effected in a temperature range of from about 700° C. to about 1000° C., and in some embodiments, from about 750° C. to about 950° C., for example, for a period of about 1 to about 3 hours.

As a result, in some embodiments, dental blank assemblies employed in methods of the present disclosure (or a portion thereof, such as the support) may need to be able to withstand a firing temperature (e.g., of a downstream or intermediate firing step) of at least about 600° C. (e.g., according to the American Dental Association's definition of an "all-ceramic" dental restoration), in some embodiments, at least about 750° C., in some embodiments, at least 800° C., in some embodiments, at least about 950° C., in some embodiments, at least about 1000° C., in some embodiments, at least about 1100° C., and in some embodiments, at least about 1200° C.

Some methods of the present disclosure can generally include the following steps:
(i) providing a first digital surface representation corresponding to a desired outer shape of a dental appliance;
(ii) forming a first article of a first material having the desired outer shape that corresponds to the first digital surface representation;
(iii) removing an inner portion of the first article to form an outer layer of the dental appliance comprising a cavity dimensioned to accommodate an inner layer;
(iv) forming a second article by filling the cavity of the first article with a second material adapted to form the inner layer, the second article still including the desired outer layer and outer shape;
(v) providing a dental object having an outer shape comprising the negative of a desired inner shape of the dental appliance;
(vi) acquiring a second digital surface representation of the outer shape of the dental object;
(vii) subtractively forming (e.g., machining) the desired inner shape in the second article (e.g., in the inner layer of the second article) that corresponds to the second digital surface representation to form the dental appliance having the desired inner shape and the desired outer shape; and
(viii) firing at least one of the first article, the outer layer, and the second article, for example, while the first article, the outer layer, or the second article is still coupled to a support (e.g., a mandrel);
for example, wherein at least one of steps (v) and (vi) can occur during or after any or all of steps (ii)-(iv), such that any or all of steps (ii)-(iv) (or even steps (i)-(iv)) can occur at least partially simultaneously with steps (v) and (vi); and wherein step (vii) occurs separately from and subsequently to steps (ii)-(iv).

Some embodiments of the methods of the present disclosure do not necessarily include all of the above steps. For example, in some embodiments, the method includes steps (i)-(iv) and (viii) above.

In some embodiments, following the above steps (i)-(viii), the method can further include step (ix) in which the dental appliance is placed in the patient's mouth.

In some embodiments, all of the above steps (i)-(ix) can be performed "chairside," such that all of the steps occur during one patient appointment or visit, e.g., at a dentist's office. In some embodiments, at least some of the above steps (e.g., any or all of steps (i)-(iv)) can be performed prior to (and potentially at a different location from) the appointment in which the remaining steps occur. The phrase "dentist's office" is used herein to generally refer to a facility or venue (e.g., a healthcare facility, a clinic, a dentist's office, an orthodontist's office, or the like) in which a patient would be prepared to receive, and would receive, a dental appliance. As such, the phrase "dentist's office" is not intended to be overly limiting, and is used only for simplicity.

The methods of the present disclosure can be "mold-free" methods, in which the outer shape and inner shape can be formed directly from the first digital surface representation and the second digital surface representation, respectively, without first creating an intermediate or temporary structure, such as a mold.

Step (i): Providing a First Digital Surface Representation

In some embodiments, step (i) above, "providing a first digital surface representation corresponding to a desired outer shape," can include performing a digital data capture of a patient's anatomy via digital impressioning (e.g., optically scanning a patient's mouth, which is described in greater detail below), or computed tomography (CT) (or computer-aided tomography (CAT)). Alternatively, the data capture can indirectly capture the patient's anatomy by performing a digital data capture of a plaster model (e.g., of the patient's mouth) or of a dental impression (e.g., of the patient's mouth), rather than directly capturing the patient's anatomy. In the case of using a dental impression, the digital data capture can be inverted from a negative volume to a positive volume. As a result, the first digital surface representation can be obtained prior to the time or date at which the remaining steps occur. Alternatively, or additionally, at least a portion of the first digital surface representation can be provided by a series of tooth libraries, or databases, that can be adaptive to replicate a portion or all of a tooth, which may be necessary for implant usage, or for a severely worn, fractured, or altogether absent tooth.

Performing a digital data capture can also be referred to as performing a digital workflow. Such a digital workflow can include optically scanning an object (e.g., a patient's mouth, a plaster model, an impression, etc.) to develop one or more digital data files (e.g., which can form, or be consolidated to form, a digital surface representation) representative of the desired dental appliance. Particularly, in step (i), the digital workflow is used to develop various images for the desired outer shape of the desired dental appliance. Such scanning can be performed using an optical scanner that is coupled to a computer-aided design (CAD) system that functions in conjunction with a computer-integrated manufacturing (CIM) system. Such a CIM system is available, for example, under the trade designation LAVA™ from 3M ESPE AG (Seefeld, Germany). Such optical scanning processes will now be described in greater detail.

In some embodiments, the first digital surface representation can be provided by a tooth library; can be known (e.g., stored in a library or in a patient's file history) from a previous digital data capture; the digital data capture can be taken at the same visit in which the patient will receive the finished dental appliance; or a combination thereof.

An example of a three-dimensional scanning system that may be employed in executing methods of the present disclosure is described in PCT Publication No. WO2009/070469 (Docket No. 63525WO003), entitled "Fabrication of Dental Articles using Digitally-controlled Reductive and Digitally-controlled Additive Processes," filed on Nov. 18, 2008, which is incorporated herein by reference in its entirety.

In the following description, the term "image" generally refers to a two-dimensional set of pixels forming a two-dimensional view of a subject within an image plane. The term "image set" generally refers to a set of related two dimensional images that might be resolved into three-dimensional data. The term "point cloud" generally refers to a three-dimensional set of points forming a three-dimensional view of the subject reconstructed from a number of two-dimensional views. In a three-dimensional image capture system, a number of such point clouds may also be registered and combined into an aggregate point cloud constructed from images captured by a moving camera. Thus it will be understood that pixels generally refer to two-dimensional data and points generally refer to three-dimensional data, unless another meaning is specifically indicated or clear from the context.

The terms "three-dimensional surface representation," "digital surface representation," "three-dimensional surface map," "three-dimensional model," and the like, as used herein, are intended to refer to any three-dimensional surface map of an object, such as a point cloud of surface data, a set of two-dimensional polygons, or any other data representing all or some of the surface of an object, as might be obtained through the capture and/or processing of three-dimensional scan data, unless a different meaning is explicitly provided or otherwise clear from the context. A "three-dimensional representation" may include any of the three-dimensional surface representations described above, as well as volumetric and other representations, unless a different meaning is explicitly provided or otherwise clear from the context.

Acquiring digital surface representation of intraoral structures is generally known. For example, U.S. Pat. No. 7,698, 014; incorporated herein by reference, describes a method of acquiring a digital surface representation of one or more intraoral surfaces and processing the digital surface representation to obtain a three-dimensional model. Such a method can be employed in the methods of the present disclosure to obtain a first digital surface representation.

As described in U.S. Pat. No. 7,698,014, FIG. 2 shows an image capture system 200 that may include a scanner 202 that captures images from a surface 206 of a subject 204, such as a dental patient, and forwards the images to a computer 208, which may include a display 210 and one or more user input devices such as a mouse 212 or a keyboard 214. The scanner 202 may also include an input or output device 216 such as a control input (e.g., button, touchpad, thumbwheel, etc.) or a display (e.g., LCD or LED display) to provide status information.

The scanner 202 may include any camera or camera system suitable for capturing images from which a three-dimensional point cloud may be recovered. For example, the scanner 202 may employ a multi-aperture system as disclosed, for example, in US Patent Publication No. 2004/0155975 to Hart et al ("Hart"). While Hart discloses one multi-aperture system, it will be appreciated that any multi-aperture system suitable for reconstructing a three-dimensional point cloud from a number of two-dimensional images may similarly be employed in the methods of the present disclosure. In one multi-aperture embodiment, the scanner 202 may include a plurality of apertures including a center aperture positioned along a center optical axis of a lens and any associated imaging hardware. The scanner 202 may also, or instead, include a stereoscopic, triscopic or other multi-camera or other configuration in which a number of cameras or optical paths are maintained in fixed relation to one another to obtain two-dimensional images of an object from a number of slightly different perspectives. The scanner 202 may include suitable processing for deriving a three-dimensional point cloud from an image set or a number of image sets, or each two-dimensional image set may be transmitted to an external processor such as contained in the computer 208 described below. In other embodiments, the scanner 202 may employ structured light, laser scanning, direct ranging, or any other technology suitable for acquiring three-dimensional data, or two-dimensional data that can be resolved into three-dimensional data.

In one embodiment, the scanner 202 is a handheld, freely positionable probe having at least one user input device 216, such as a button, lever, dial, thumb wheel, switch, or the like, for user control of the image capture system 200 such as starting and stopping scans. In an embodiment, the scanner 202 may be shaped and sized for dental scanning. More particularly, the scanner may be shaped and sized for intraoral scanning and data capture, such as by insertion into a mouth of an imaging subject and passing over an intraoral surface 206 at a suitable distance to acquire surface data from teeth, gums, and so forth. The scanner 202 may, through such a continuous acquisition process, capture a point cloud of surface data having sufficient spatial resolution and accuracy to prepare a dental model, either directly or through a variety of intermediate processing steps.

Although not shown in FIG. 2, it will be appreciated that a number of supplemental lighting systems may be employed during image capture. For example, environmental illumination may be enhanced with one or more spotlights illuminating the subject 204 to speed image acquisition and improve depth of field (or spatial resolution depth). The scanner 202 may also, or instead, include a strobe, flash, or other light source to supplement illumination of the subject 204 during image acquisition.

The computer 208 may be, for example, a personal computer or other processing device. In one embodiment, the computer 208 includes a personal computer with a dual 2.8 GHz Opteron central processing unit, 2 gigabytes of random access memory, a TYAN Thunder K8WE motherboard, and a 250 gigabyte, 10,000 rpm hard drive. This system may be operated to capture approximately 1,500 points per image set in real time using the techniques described herein, and store an aggregated point cloud of over one million points. As used herein, the term "real time" means generally with no observable latency between processing and display. In a video-based scanning system, real time more specifically refers to processing within the time between frames of video data, which may vary according to specific video technologies between about fifteen frames per second and about thirty frames per second. More generally, processing capabilities of the computer 208 may vary according to the size of the subject 204, the speed of image acquisition, and the desired spatial resolution of three-dimensional points. The computer 208 may also include peripheral devices such as a keyboard 214, display 210, and mouse 212 for user interaction with the camera system 200. The display 210 may be a touch screen display capable of receiving user input through direct, physical interaction with the display 210.

Communications between the computer 208 and the scanner 202 may use any suitable communications link including, for example, a wired connection or a wireless connection based upon, for example, IEEE 802.11 (also known as wireless Ethernet), BlueTooth, or any other suitable wireless standard using, e.g., a radio frequency, infrared, or other wireless communication medium. In medical imaging or other sensitive applications, wireless image transmission from the scanner 202 to the computer 208 may be secured. The computer 208 may generate control signals to the scanner 202 which, in addition to image acquisition commands, may include conventional camera controls such as focus or zoom.

In an example of general operation of a three-dimensional image capture system 200, the scanner 202 may acquire two-dimensional image sets at a video rate while the scanner 202 is passed over a surface of the subject. The two-dimensional image sets may be forwarded to the computer 208 for derivation of three-dimensional point clouds. The three-dimensional data for each newly acquired two-dimensional image set may be derived and fitted or "stitched" to existing three-dimensional data using a number of different techniques. Such a system employs camera motion estimation to avoid the need for independent tracking of the position of the scanner 202. One useful example of such a technique is described in commonly-owned U.S. Pat. No. 7,605,817, incorporated herein by reference. However, it will be appreciated that this example is not limiting, and that the principles described herein may be applied to a wide range of three-dimensional image capture systems.

The display 210 may include any display suitable for video or other rate rendering at a level of detail corresponding to the acquired data. Suitable displays include cathode ray tube displays, liquid crystal displays, light emitting diode displays and the like. In some embodiments, the display may include a touch screen interface using, for example capacitive, resistive, or surface acoustic wave (also referred to as dispersive signal) touch screen technologies, or any other suitable technology for sensing physical interaction with the display 210.

The digital surface representation may be processed with one or more post-processing steps. This may include a variety of data enhancement processes, quality control processes, visual inspection, and so forth. Post-processing steps may be performed at a remote post-processing center or other computer facility capable of post-processing the imaging file, which may be, for example a dental laboratory. In some cases, this post-processing may be performed by the image capture system 200. Post-processing may involve any number of clean-up steps, including the filling of holes, removing of outliers, etc.

Data enhancement may include, for example, smoothing, truncation, extrapolation, interpolation, and any other suitable processes for improving the quality of the digital surface representation or improving its suitability for an intended purpose. In addition, spatial resolution may be enhanced using various post-processing techniques. Other enhancements may include modifications to the data, such as forming the digital surface representation into a closed surface by virtually providing a base for each arch, or otherwise preparing the digital surface representation for subsequent fabrication steps.

As a result, such an above-described digital workflow includes scanning to capture a three-dimensional representation of some or all of the dentition of a patient's intraoral surfaces, at least at the desired location, i.e. typically the tooth structures directly adjacent those that will come in contact with the dental appliance that will be placed in the patient's mouth. This can sometimes be referred to as capturing the "pre-op" condition, and can include capturing a representation of soft tissue as well as dentition.

As mentioned above, in some embodiments, at least a portion of a tooth may be missing or broken. In such cases, a library of tooth forms for each human tooth (e.g., the first molar) may be provided by software and used to form the first digital surface representation, or merged with any acquired digital data files to form the first digital surface representation.

Thus, the digital surface representations may be created by consolidating or merging various digital data files (e.g., including data files acquired by optically scanning and/or data files previously acquired and/or provided by tooth libraries), and the digital data files or the resulting digital surface representation can be transmitted to a rapid fabrication facility such as a dental laboratory, an in-house dental laboratory at a dentist's office, or any other facility with machinery to fabricate physical models from digital models. In yet another embodiment, the digital surface representations may be downloaded from an internet site.

Any suitable optical scanner that can perform the above-described optical scanning procedures can be employed in step (i) of the method. Two exemplary optical scanners include a Cerec System, available from Sirona Dental Systems (Germany), and an E4D Dentist Chairside CAD/CAM System, available from D4D Technologies (Richardson, Tex.).

Providing the first digital surface representation can also include some of the above-described steps that include consolidating various data files or images and/or designing the outer contours, i.e., the "digital surface representation" representative of the "outer shape" of the desired dental appliance. Such designing of the final desired outer shape can be performed by, or can be completed using input from, the dentist (or dental practitioner), for example, and can include at least some of the above-described processing, post-processing, and/or data enhancement steps. That is, such finalizing can include manipulating the digital surface representation using software tools to alter the shape, size, positioning, and/or relationship to adjacent and antagonist teeth, of all or a part of the dental appliance. Such manipulation can be performed by a dental practitioner (e.g., a dentist, a dental assistant, a dental lab technician, or other suitable dental practitioner). Alternatively, the digital surface representation formed by combining digital data files can be used without modification (which can be referred to as a "clone" in some software programs). In some embodiments, such finalizing or manipulation of the digital surface representation that is representative of the desired outer shape of the desired dental appliance can be considered to be a part of step (ii), "forming a first article having the desired outer shape."

The first digital surface representation can include information relating to the outer surface or outermost shape, as well as information regarding the inner cavity shape of the outer layer, such as thickness of the outer shape, any internal mammelon structure, or any other information relating to desired inner surfaces of the outer layer (or, said another way, the desired outer surfaces of the inner layer of the desired dental appliance). Generally, information relating to internal mammelon structure and/or optical properties can be input into the model manually when designing the desired outer layer, for example, by comparing color chips, using a color camera, choosing colors from libraries or databases, etc.

As a result, the step of providing a first digital surface representation can also include providing the above information regarding the desired outer layer (or, equivalently, the desired inner layer) as digital data files, and merging such digital data files with any data files regarding the desired outer shape to form the first digital surface representation. Such additional information relating to the color, shading, and/or translucency, as well as the depth of any such parameters, can be provided by one or more libraries, or a patient's file history.

Such specific design characteristics may be unique for each tooth. For example, a front incisor may be different from a rear molar. For a two-layer dental appliance, this design information can determine the thickness of the outer layer at each point on the dental appliance. For example, the outer layer of the dental appliance may be thicker near the occlusal surface than it is near the gingival margin.

Alternatively, the outer layer may simply be set (and the first digital surface representation adjusted accordingly) to a uniform thickness, such as 1 mm or 2 mm. Software, particularly CAD/CAM software associated with a fabrication tool, can allow a dental practitioner to select between uniform thickness of the outer layer, thickness information from a library or database, to use software tools to customize and design the thickness of the outer layer at various points on the dental appliance, or a combination thereof.

Step (ii): Forming a First Article of a First Material Having the Desired Outer Shape Step (ii) above, "forming a first article of a first material having the desired outer shape that corresponds to the first digital surface representation" can include transmitting the first digital surface representation to an appropriate fabrication tool, and using computer-aided manufacturing (CAM) software to translate the first digital surface representation into tooling motions, speeds, tool types (e.g., burr sizes and shapes for subtractive methods), and the like, to form the desired outer shape of the desired dental appliance, based on the first digital surface representation. The resulting preparation that includes only a portion (e.g., the desired outer shape) of the desired dental appliance can be referred to as a first "article," "preparation," or "intermediate."

The desired outer shape can be obtained using additive methods (e.g., building up material, such as by three-dimensional ("3D") printing, rapid-prototyping, selective laser sintering, stereolithography, other suitable additive methods, or a combination thereof); subtractive methods (e.g., machining from a mill block); or a combination thereof. For example, a mill block can be milled using a LAVA™ computer-integrated manufacturing system from 3M ESPE AG (Seefeld, Germany). In some embodiments, full chairside systems can be employed that include a scanner, software, and one or more mills, such as the Cerec System available from Sirona (Germany) and the E4D System available from D4D (Richardson, Tex.).

In embodiments in which the first article having the desired outer shape is prepared according to a subtractive process, such as milling, the first article can remain attached to a support (e.g., a mandrel or frame, e.g., by a sprue) to facilitate indexing and registering the first article in the fabrication tool for later removing a portion (i.e., an inner portion) of the first article and forming the desired inner shape. As a result, step (ii) can also include providing a first assembly comprising the first article coupled to a support. In some embodiments (e.g., a "chairside" process, or a "single-appointment" or "same day" process), the entire outer layer can be formed in the same tool (e.g., mill), and the first article (or first assembly) can simply remain mounted in the fabrication tool after step (ii), and the cavity can then be formed in the first article (i.e., in step (iii)). In some embodiments, the first article can be considered to include the sprue, or to be coupled to the sprue. In some embodiments, at the completion of step (ii), the inner structures, thickness, and the like, of the outer layer may not yet be known, and the first article can remain relatively "block-like" and oversized.

In some embodiments, the first article can be polished, for example, using a hand tool.

For layered, biomimetic and/or multi-chromatic dental appliances, such as dental restorations, the first material (e.g., the mill block used in subtractive methods) can be relatively hard and/or translucent relative to the second material, for example, to simulate an enamel layer.

In some embodiments, the first material can be formed of materials that are generally classified as a "ceramic," including, but not limited to, one or more of glasses, glass-ceramics, porcelains, ceramics, and combinations thereof. For example, when subtractive methods are employed, the blank from which the desired outer shape is milled can be formed of a glass material, a glass-ceramic material, a porcelain material, a ceramic material, or a combination thereof. Such materials can be milled in a timeframe that would allow the method to be performed "chairside," or in a "single-appointment" or "same day" process.

While ceramic-based materials such as those listed above can require somewhat time-consuming machining and/or firing steps, it is still conceivable that all of steps (i)-(ix) can be performed chairside when such materials are employed.

Examples of glasses that can be employed as the first material (e.g., as the blank of a dental blank assembly) of the present disclosure include, but are not limited to, silica, borosilicate, sodium oxide, potassium oxide, calcium oxide, flint glass, soda-lime glass, other suitable glasses, or combinations thereof.

Examples of glass-ceramics that can be employed as the first material (e.g., as the blank of a dental blank assembly) of the present disclosure include, but are not limited to, lithium disilicate, leucite-reinforced glass-ceramics, and combinations thereof. Other examples of suitable glass-ceramic materials that can be employed include, but are not limited to, Vita Mark II (available from Vita Zahnfabrik, Germany), Empress CAD (available from Ivoclar Vivadent, Lichtenstein), Paradigm C (available from 3M ESPE, Seefeld, Germany), E-Max CAD (Ivoclar Vivadent), other suitable glass-ceramic materials, or combinations thereof.

Examples of porcelains that can be employed as the first material (e.g., as the blank of a dental blank assembly) of the present disclosure include, but are not limited to, feldspathic porcelains.

Examples of ceramics that can be employed as the first material (e.g., as the blank of a dental blank assembly) of the present disclosure include, but are not limited to, zirconia ($ZrO_2$), alumina ($Al_2O_3$), spinel ($MgAl_2O_4$), leucite (e.g., chemically-derived, such as that described in U.S. Pat. No. 5,622,551), and combinations thereof.

In some embodiments, the first material can be provided by the blank of a fireable dental blank assembly. Various details of such dental blank assemblies are described in greater detail below, with reference to FIGS. 1-5.

Step (iii): Removing an Inner Portion of the First Article to Form an Outer Layer of the Dental Appliance Step (iii), "removing an inner portion of the first article to form an outer layer of the dental appliance comprising a cavity dimensioned to accommodate an inner layer," can also sometimes be referred to as milling an internal cutback of the first article. This step in the workflow can generally include transmitting information regarding the desired contours and outer layer thickness (which can be uniform or can vary at different locations on the appliance, as described above) to a fabrication tool via CAM software that can translate the data into tooling motions, speeds, tool types, etc. As mentioned above, such information can form a portion of, or be included in, the first digital surface representation. In some embodiments, however, such information can be provided to the fabrication tool separately from the first digital surface representation. For example, in some embodiments, the additional information can be a "second digital surface representation" that needs to be merged and reconciled with the first digital surface representation to form a first three-dimensional digital representation comprising all of the information regarding the outer layer. In such embodiments, the second digital surface representation described above as being acquired in step (vi) can be referred to as a "third digital surface representation," which can be merged (and registered) with the first three-dimensional digital representation to form a second three-dimensional digital representation that includes the details of the outer layer and the inner layer, including the desired outer shape of the dental appliance, as well as the desired inner shape of the dental appliance.

In some embodiments, removing a portion (e.g., an inner portion) of the first article can include removing a substantial portion of the first article, such that the resulting product is in the form of a relatively thin shell that can form the outermost portion of the desired dental appliance. For example, in some embodiments, "removing a substantial portion" of the first article can include removing more than 40% by volume (i.e., 40 vol %) of the first article, in some embodiments, more than 50% by volume, in some embodiments, more than 60% by volume, and in some embodiments, more than 75% by volume. Removing a substantial portion of the first article can also be defined by whether a substantially different second article was formed when a portion of the first article was removed and the resulting cavity was filled with a second material (the process for which is described in greater detail below). In some embodiments, e.g., with respect to a biomimetic dental appliance, a "substantially different" second article can generally refer to a second article that has a statistically significantly different material property, as compared to the first article (e.g., before any portion was removed), when tested according to standard testing methods for a particular material property of interest. In addition, in some embodiments, e.g., with respect to a multi-chromatic dental appliance, a "substantially different" second article can generally refer to a second article that is visually distinguishable (e.g., by the naked human eye) from the first article (e.g., before any portion was removed).

In some embodiments, this step can be performed by (a) inserting the first article into the same type of machine in which the first article was prepared (i.e., accommodating the same support (e.g., mandrel) and having compatibility with the same data files), if the first article was prepared by the same method and prepared at a different location, in a different machine; (b) inserting the first article into the same machine (e.g., if the first article was formed at the same location—either at the dentist's office, or in another location); or (c) forming the cavity of the desired outer layer in the first article that is still residing in the machine in which the outer shape was formed (e.g., if the entire process is chairside and the first article was never removed from the machine in which the outer shape was formed).

The fabrication tool can then subtractively form the outer layer by forming a cavity in the first article that will eventually be filled with a second material that can have a different material and/or optical property than the first material of which the first article is formed. The second material can be formed of any of the materials described above that are generally classified as "ceramic" materials, include glasses, glass-ceramics, porcelains, ceramics, and combinations thereof, such as those described above with respect to the first material.

The outer layer, or shell, formed by step (iii) can still be attached to a support (e.g., the same support to which the blank and the first article were attached, e.g., by a sprue) to facilitate indexing and registering the outer layer in the fabrication tool. As a result, step (iii) can also include providing a second assembly comprising the outer layer coupled to a support.

In some embodiments, steps (ii) and (iii) above can be done simultaneously. For example, steps (ii) and (iii) can be performed simultaneously in embodiments in which the first digital surface representation includes all of the information necessary to form the complete outer layer, which can include, for example, the desired (e.g., final) outer shape of the dental appliance, along with the desired internal cavity shape (e.g., any internal mammelon structure(s)), the thickness of the outer layer, etc.

Step (iv): Forming a Second Article by Filling the Cavity of the First Article with a Second Material Adapted to Form the Inner Layer The outer layer formed in steps (ii) and (iii) having a desired outer shape (i.e., surface) and a cavity having a desired inner shape (e.g., including any desired mammelon structure, or having a nonspecific surface such that the outer layer has a generally uniform thickness) can then be filled with a second material in step (iv) to form a second article. That is, the interior cavity of the first article can be filled with a second material to form a second article having the desired outer shape, and the desired outer layer. The second article also includes an inner layer having a desired outer shape, which can be the desired inner cavity shape of the outer layer, or which can be sized to accommodate any intermediate layers (or an adhesive) between the two layers. The inner layer will later be further processed to include an overall desired inner shape of the dental appliance. At this stage, however, the second article generally only includes the desired outer shape of the inner layer, and does not yet include the desired inner shape of the dental appliance.

As mentioned above, in some embodiments, the method of the present disclosure can include steps (i)-(iv) and (viii), such that an exemplary method of the present disclosure can include steps (i)-(iv) and (viii) only, the resulting product being an anatomical (and, optionally, multi-chromatic and/or biomimetic), multi-layer intermediate dental appliance capable of being further processed, as desired, depending on specific patient circumstances. Such a resulting intermediate (e.g., the second article) can include or be coupled to a support (e.g., a third assembly) to facilitate downstream processing.

In embodiments in which the second article having the desired outer shape is prepared according to a subtractive process, such as milling, the second article can remain attached to a support (e.g., mandrel or frame, e.g., by a sprue) to facilitate indexing and registering the second article in the fabrication tool for later forming the desired inner shape (e.g., for accommodating a tooth stump, an implant, an implant abutment, healing cap, or the like, or combinations thereof). As a result, step (iv) can also include providing a third assembly comprising the second article coupled to a support.

In some embodiments (e.g., a "chairside" process, or a "single-appointment" or "same day" process), the second article can simply remain mounted in the fabrication tool, and the inner shape can be formed in the same tool in which the outer shape was formed. The second article can either be considered to include the sprue, or to be coupled to the sprue. At this point in time, the lower portion of the second article (e.g., subgingival portion) may not yet be known and can remain relatively "block-like" and oversized, to be finalized later in the process. It should be noted that the term "lower" is relative and depends on the orientation of the second article.

As mentioned above, the second material can be formed of any of the ceramic-based materials, including glasses, glass-ceramics, porcelains, and/or ceramics described above with respect to the first material. In some embodiments, the second material can include a different material and/or optical property than the first material. In some embodiments, the second material can be flowable in order to fill the cavity of the outer layer (e.g. a slurry formed from a powder and liquid), and can then be fired, for example, while coupled to the support. If the second material is a slurry, care must be taken to prevent the slurry from spilling out of the cavity in the first article during subsequent handling steps. As a result, in some embodiments, the filling step can also include a firing step, as described below in step (viii).

In some cases, step (iv) includes multiple filling and firing steps, such that the second material can be positioned in the cavity of the first article layer-by-layer (e.g., employing thinner layers) to compensate for possible shrinkage and to allow for relatively brief individual firing steps.

In some embodiments, the second material can be formed of a glass, glass-ceramic, porcelain and/or ceramic which has been pre-fired and milled, e.g. from a mill blank, to fit within the cavity of the outer layer. This material would then be inserted and cemented to the first article. If this technique is used, the outer layer may not include undercuts that would prevent complete insertion of the pre-formed inner layer.

As a result, in the methods of the present disclosure, the second material (which forms a layer of the dental appliance and which generally does not include or refer to any adhesive or bonding layer used to couple the dental appliance to a dental object and/or to couple together layers of the dental appliance) can be positioned in the cavity of the outer layer, and then hardened (e.g., by firing) to form the second article, which can be further processed (e.g., subtractively, such as by machining) to form the desired inner shape of the dental appliance to accommodate a dental object. Alternatively, the second material can be hardened and shaped (e.g., by machining, such as milling) prior to being positioned in the cavity of the outer layer, and then coupled to the inside of the outer layer, for example, using an adhesive (or other bonding material or layer) and, optionally, a firing step. However, an adhesive that is pressed into place between the second material and the dental object, or between the first and second materials would not generally fall within the scope of creating an anatomical, multi-chromatic or biomimetic dental appliance. However, the adhesive used can also fall within the general "ceramic" class of materials, such that the resulting dental appliance can still be "all-ceramic."

It can be important for the first material and the second material to be compatible, particularly, in embodiments in which the first material is directly bonded to the second material, such that the resulting dental appliance has structural integrity and the first and second materials appropriately bond to one another.

For example, in some embodiments, it can be important to match the coefficient of thermal expansion (CTE) of the first material with that of a second material. Otherwise, in some cases, the first material and the second material may not be fused correctly during firing which might lead to failure of the restoration. In some embodiments, glass itself (e.g., including some of the formulations listed above) may match that of zirconia. Adding leucite to glass can raise the CTE of the glass, and can also improve the mechanical strength of the glass, but crystal materials other than leucite can also be used. The amount of leucite (or other crystal phase) to be added to the glass can depend on the material makeup of the other material (e.g., the second or first material) to which the first or second material will be coupled (e.g., fused). Alumina has a lower CTE compared to zirconia so the glass can be adapted in its composition to reach this lower CTE (e.g. Vita VM7 (VM9 can be used for zirconia, for example), Vita Zahnfabrik, Germany or Vident, USA).

Table 1 lists exemplary pairings of first materials, second materials, and cements (or bonding material or layer) that can be used to join the first and second materials of the present disclosure. The cements are shown by way of example only; however, it should be understood that in some embodiments, an adhesive is not necessary, because the first material and the second material can be directly bonded or fused together without such an adhesive (e.g., if the second material is used to fill the cavity in the outer layer and then fired). Table 1 is only intended to be illustrative and not limiting:

TABLE 1

Exemplary pairings of first materials and second materials*

| First/Second Material | Second/First Material | Bonding Layer (if employed) |
|---|---|---|
| Zirconia[1] | Lithium disilicate[2] | Feldspathic porcelain[3] |
| Zirconia[1] | Feldspathic porcelain[4] | Feldspathic porcelain[5] |
| Zirconia[1] | Glass (e.g., $SiO_2$ with $Al_2O_3$, $K_2O$, $Na_2O$, etc.) | Glass solder (e.g., $SiO_2$ with $Al_2O_3$, $K_2O$, $Na_2O$, etc.) |
| Alumina[6] | Glass (e.g., $SiO_2$ with $Al_2O_3$, $K_2O$, $Na_2O$, etc.); or Glass ceramic[7] | Glass (e.g., $SiO_2$ with $Al_2O_3$, $K_2O$, $Na_2O$, etc.); or Glass ceramic[7] |
| Lithium disilicate[2] | Feldspathic porcelain[4] | Fusion Porcelain[8] |
| Lithium disilicate[2] | Zirconia[1] | Feldspathic porcelain[3] |

*First and second materials are interchangeable; that is, the materials listed as first materials can instead be second materials, and the materials listed as second materials can instead be first materials.
[1] e.g., from 3M ESPE, Seefeld, Germany
[2] e.g., E MAX CAD, available from Ivoclar Vivadent, Amherst, NY
[3] e.g., LAVA ™ Ceram Shoulder Porcelain, available from 3M ESPE
[4] e.g., VITA Mk II, available from Vita Zahnfabrik, Germany or Vident, USA
[5] e.g., VITA VM9, available from Vita Zahnfabrik, Germany or Vident, USA
[6] e.g., VITA alumina, available from Vita Zahnfabrik, Germany or Vident, USA
[7] e.g., VITA VM7, available from Vita Zahnfabrik, Germany or Vident, USA
[8] e.g., LAVA ™ DVS Fusion Porcelain, available from 3M ESPE In embodiments in which the inner layer is pre-formed, the inner layer precursor can be formed according to similar methods used to form the outer shape of the first article. The outer shape of the inner layer can correspond directly to the desired inner cavity shape of the outer layer, or it can be sized to accommodate any intermediate layers, or an adhesive or bonding layer. The inner layer can then be positioned in the cavity of the first article and adhered (e.g., via a adhesive or adhesive) or otherwise affixed in place to form the second article.

Furthermore, in embodiments employing a pre-formed (e.g., rigid, solid, etc.) inner layer (e.g., formed of a sintered or pre-sintered material), the cavity of the outer layer may include no undercuts that might prevent complete insertion of the inner layer. For example, the cavity can include a substantially uniform shape, or even a shape that tapers to a narrower shape toward the occlusal surface to facilitate coupling a pre-formed inner layer into the outer layer to form the second article. Alternatively, in some embodiments, the inner layer can be formed to be slightly smaller than the cavity of the outer layer, which can allow the inner layer to be pushed into a layer of adhesive, followed by a firing step to fire the adhesive sandwiched between the outer layer and the inner layer, and possibly to additionally sinter the inner layer, e.g., if the inner layer was previously only pre-sintered.

In some embodiments, the preceding steps (i.e., at least one of steps (i)-(iv) and (viii) of the method described above) can be performed "off-site" and prior to the patient's visit during which the remaining steps occur. For example, in the situation where the first digital surface representation is acquired, at least partially, from one or more tooth libraries (or the patient's file history), the first article can be formed in an "off-site" manufacturing or laboratory setting, based on the first digital surface representation. Then, when the patient comes to the dentist's office to receive his/her dental appliance (e.g., a crown), the remaining steps (iii)-(vii), (iii)-(viii), or (iii)-(vi) and (ix) can be performed, using the first article (i.e., first assembly) that was previously created. Alternatively, in some embodiments, steps (i)-(iv) and (viii) can all be performed "off-site" and prior to the patient's visit. Then, when the patient comes to his/her appointment to receive his/her dental appliance, the remaining steps (v)-(vii), (v)-(viii), or (v)-(vii) and (ix) can be performed, using the second article (i.e., third assembly) that was previously created. In such embodiments, at least some of the steps would be considered to be performed "chairside." However, in some embodiments, all of the steps (i)-(ix) can be performed during one patient visit to the dentist's office, in which case, the entire process would be considered to be "chairside." In some embodiments, whether the entire process is completed sequentially at one location or some of the steps are completed at a different time (and potentially, at a different location), can be determined at least partially by the materials used to form the dental appliance.

Step (v): Providing a Dental Object Having an Outer Shape Comprising the Negative of the Desired Inner Shape of the Dental Appliance Step (v) of the method, "providing a dental object having an outer shape comprising the negative (e.g., volumetric inverse) of the desired inner shape of the dental appliance," can include preparing a tooth by removing carious parts of the tooth to be restored, leaving behind a tooth stump to receive the dental appliance (e.g., a crown; in the case of bridges, more than one tooth stump and pontic sites may receive the dental appliance); providing or preparing an implant, e.g., by coupling an implant abutment which will receive the dental appliance to a previously implanted dental implant; providing other suitable dental objects; or combinations thereof.

Step (vi): Acquiring a Second Digital Surface Representation of the Outer Shape of the Dental Object Step (vi) of the method, "acquiring a second digital surface representation of the outer shape of the dental object," can include any of the above-described optical scanning steps to capture digital data files representative of the dental object and create a second digital surface representation (e.g., by using CAD/CAM software to convert the digital data files to a three-dimensional model).

In some embodiments, step (vi) can also include inverting the second digital surface representation from a positive-volume digital surface representation of the dental object to a negative-volume digital surface representation to be formed (e.g., subtractively) in the second article.

In some embodiments, step (vi) can further include marking the gingival margin (e.g., using the CAD/CAM software), which can be done manually by the dental practitioner (e.g., dentist, assistant, dental lab technician, etc.). The CAD/CAM software tools can be used to create a "boundary" for the finished dental appliance.

Step (vi) can also include merging the first and second digital surface representations (e.g., using CAD/CAM software) to register, align, orient, and/or superimpose the two three-dimensional models relative to one another. The first and second digital surface representations can be registered, for example, by triangulating the positions of the dental objected (e.g., the tooth stump) within the digital surface representation of the first article (i.e., the dental appliance with only the desired outer shape but not yet the desired inner shape). This can be accomplished, for example, by aligning duplicate and unaltered points, such as digital surface representations of adjacent teeth or structures in the patient's mouth, from the first and second digital surface representations. In some embodiments, the second digital surface representation can itself include one or more indexing or reference points to assist in orienting or registering the second digital surface representation with the first digital surface representation when the two digital surface representations are merged.

In addition, in some embodiments, step (vi) can further include digitally designing the desired inner shape of the dental appliance to match (i.e., fit within) the already formed outer shape of the first article. Such designing can include any of the steps described above with respect to designing, refining or finalizing the first digital surface representation, and can further include translating a marked margin (if applicable) to a lower "boundary" of the finished dental appliance, and/or designing a gap or offset between the first digital surface representation and the second digital surface representation in the final merged three-dimensional digital representation to accommodate a layer of adhesive, for example.

The first and second digital surface representations can be stored at the stages of the process in which they are either provided or created, which can be at different times and at different locations. The first and second digital surface representations can then later be merged or meshed together to create a final three-dimensional model of the desired dental appliance.

In some embodiments, if the first digital surface representation is no longer available, another (e.g., a third) digital surface representation can be acquired by digital capturing (e.g., by optically scanning) the second article, which already includes the desired outer shape of the desired dental appliance. The third digital surface representation can then act as the first digital surface representation in the description above for the merging and registering the inner and outer digital surface representations of the desired dental appliance.

Step (vii): Forming the Desired Inner Shape

Step (vii), "forming the desired inner shape," can include subtractively forming the desired inner shape in the second article (i.e., third assembly comprising the second article coupled to a support) from the second digital surface representation. In some embodiments, the desired inner shape can be formed entirely in the inner layer of the second article; although, it is possible that the inner shape could extend at least slightly into the outer layer as well. In some embodiments, this step can be performed by (a) inserting the second article into the same type of machine in which the first article and/or outer layer were prepared (i.e., accommodating the same support and having compatibility with the same data files), if the first article and/or outer layer was prepared by the same method and prepared at a different location, in a different machine; or (b) remounting the second article (i.e., third assembly) into the same machine (e.g., if the first article and/or outer layer was formed at the same location—either at the dentist's office, or in another location) after the second material has been positioned in the cavity of the outer layer.

The CAD/CAM software can direct the machine to subtractively form the desired inner shape in the second article, based on the steps performed in step (v), to form a dental appliance having a desired inner shape and a desired outer shape. In addition, the lower portion of the second article can simultaneously be machined to match the margin and to achieve a dental appliance of an appropriate size (e.g., height).

Step (viii): Firing at Least One of the First Article, the Outer Layer, and the Second Article Step (viii), "firing at least one of the first article, the outer layer, and the second article," can include firing at least one of the first article, the outer layer, and the second article while such articles or layers are still coupled to a support that is configured to withstand the temperatures necessary to fire these articles. As mentioned above, methods of the present disclosure can include providing a dental blank assembly comprising a blank coupled to a support, and forming the first article can include providing a first assembly comprising the first article coupled to the support. Additionally, forming the outer layer can include providing a second assembly comprising the outer layer coupled to the support, and forming the second article can include providing a third assembly comprising the second article coupled to the support. The details (e.g., temperatures and durations) of such firing steps can be dependent upon the materials used for the first material and the second material. For example, higher temperatures and longer durations may be necessary to fire ceramics than what is necessary to fire glasses, glass-ceramics, or porcelains. In addition, as mentioned above, in some embodiments, the inner layer formed of the second material can be formed separately (i.e., pre-formed), and can be pre-sintered or fully sintered. However, in some embodiments, attaching the inner layer into the outer layer (e.g., that is still coupled to the support) can include a firing step, and the support would need to be able to withstand such a firing step as well.

While the firing steps used will be determined by the materials used and one of skill in the art will understand to fire the materials according to the manufacturer's specifications, the firing steps of the present disclosure used to fire at least one of the first article (i.e., first assembly), the outer layer (i.e., second assembly), and the second article (i.e., third assembly) can be performed at any of the firing temperatures described above.

Step (ix): Place the Dental Appliance in the Patient's Mouth

Step (ix), "placing the dental appliance in the patient's mouth," can include cutting the dental appliance away from the sprue (i.e., the support), any final firing steps (e.g., for crystallization, staining, and glazing), any final polishing steps (e.g., before or after placement in the patient's mouth), and/or any necessary coupling (e.g., adhesive, curing, etc.) steps for positioning the dental appliance in the patient's mouth (e.g., coupling to a tooth stump or implant abutment). In some embodiments, at least some of the polishing, staining, glazing, firing, or other finishing steps can occur while the dental appliance is still coupled to the support.

The process of staining and/or glazing a dental appliance (e.g., a dental restoration) can include treating the outside of the appliance (e.g., a glass-ceramic restoration) to achieve a more natural appearance. Staining and glazing materials can be applied using a brush and then the dental appliance can be fired (e.g., at 750-1000° C.). In some embodiments, this process includes at least two steps: at least one for staining (which generally refers to shaded material), and at least one for glazing (which generally refers to translucent material).

The dental appliance can be affixed to the dental object (e.g., prepared tooth stump, implant abutment, etc.) with a dental cement or adhesive (e.g., inorganic), as known in the art. For example, the cavity (i.e., the cavity defined at least partially by the desired inner shape) of the dental appliance can be partially filled with a dental adhesive and then placed over the dental object, such that the base of the dental appliance contacts the necessary structures or tissues in the patient's mouth. Suitable dental cements are commercially available from 3M ESPE under the trade designation "RelyX Unicem Self Adhesive Universal Resin Adhesive."

In some embodiments, the dental appliance having the desired inner shape and desired outer shape can be fired, which may produce a more durable, harder appliance. Such a firing step can be done relatively quickly, e.g., in some embodiments, such a firing step can be performed in less than 30 minutes.

As mentioned above, at least one of steps (i)-(iv) and (viii) can be performed prior to the patient visit, and even at a different location. In embodiments in which the first article (i.e., first assembly), the outer layer (i.e., the second assembly), and/or the second article (i.e., the third assembly) is formed "off-site," for example, at a dental laboratory, the machining equipment used in the dental laboratory can be compatible with the machining equipment used at the dentist's office, for completion of steps (v)-(vii), such that both devices use the same support and mill blank. Such a support can serve as an indexing feature to ensure that the inner shape is formed with the correct orientation, alignment, and relative positioning with respect to the outer shape. In such cases, the first article (and/or the second article) can be coupled to, or include, a sprue when it is provided to the dentist's office for the remaining steps. Conceivably, any remaining machining or finalizing (e.g., polishing, etc.) steps can also be performed off-site if the second digital surface representation is electronically transmitted to the dental laboratory. If the dental laboratory is geographically close to the dentist's office, this could conceivably still result in the entire process essentially being a chairside, or "single-appointment" or "same day" process.

As mentioned above, the dental appliance can include a variety of dental restorations, abutments, etc. Therefore, in some embodiments, the dental appliance can include a dental crown designed to be fit over a tooth stump or implant abutment. However, in some embodiments, the dental appliance can include a bridge. The methods of the present disclosure can be especially valuable for bridges, which may take a long time to mill, finish and polish the extensive outer surfaces as compared to a single unit crown. For example, a bridge can be designed and formed comprising three (or more) units, in which the two end units are each designed to fit over a tooth stump or implant abutment, with one or more solid pontics in between. In such embodiments, the outer shape can include the outer shape of the entire bridge (or the outer layer, including the desired outer shape and the desired inner cavity shape of the outer layer, can include the outer layer of the entire bridge), and the workflow can include one or more second digital surface representations, each corresponding to a dental object. By way of further example, one dental object could be a tooth stump, and one could be an implant abutment. The one or more inner shapes corresponding to the one or more second digital surface representations can be formed simultaneously or sequentially without departing from the spirit and scope of the present disclosure.

The method described above is broken into nine steps by way of simplicity and clarity. However, it should be understood that this breakdown of the methods and workflows of the present disclosure are by way of example only, and the method can instead include more or fewer steps than those outlined above. For example, step (vi) ("acquiring a second digital surface representation") is described above as including, in some embodiments, the steps of merging the first digital surface representation and the second digital surface representation and designing a three-dimension digital representation of the desired dental appliance. However, it should be understood, for example, that such steps can actually be thought of as additional steps in the methods of the present disclosure, and need not be considered to be a part of step (vi). Furthermore, such additional steps may actually be performed as a part of a different step, such as step (vii) ("forming the desired inner shape"), or may be combined in a different way. As a result, the present disclosure is not limited to the steps described above, or to the separation of steps described above.

The methods of the present disclosure can also include the step of providing a dental blank assembly that comprises a blank and a support coupled together and configured to withstand downstream firing processes (e.g., which may be employed in the formation of multilayer all-ceramic dental appliances). Additional details of such dental blank assemblies will now be described in greater detail with reference to FIGS. 1-5.

Dental Blank Assemblies

As described above, the dental blank assemblies of the present disclosure generally include a blank and a support coupled together. The dental blank assembly can also include a means for coupling the blank and the support, and the means for coupling the blank and the support can also be configured to withstand the firing temperatures. Furthermore, the blank, the support, and the coupling means can each be configured to mechanically withstand downstream machining processes, such as milling, so that the dental blank assembly as a whole has the mechanical integrity necessary to withstand downstream machining process(es). In this way, the blank can remain securely and reliably coupled to the support throughout machining of the blank, and formation of the desired multilayer dental appliance. In some embodiments, the support and the blank can be formed of different materials. Alternatively, in some embodiments, the dental blank assembly can include a unitary construction, where the blank and the support are integrally formed from the same material.

FIGS. 1-2 illustrate a dental blank assembly 100 according to one embodiment of the present disclosure. As shown in FIGS. 1-2, the dental blank assembly 100 can include a blank 102, a support 104 and a means 106 for coupling the blank 102 and the support 104. As shown in FIG. 2, in some embodiments, the means 106 for coupling the blank 102 and the support 104 can include a bonding composition 108. In some embodiments, the bonding composition 108 can be referred to as a "bonding layer" which can further be described as comprising, consisting of, or consisting essentially of the bonding composition 108. The bonding composition 108 is described in greater detail below.

The support 104 can be formed of at least one of a high melting point metal or metal alloy, and a ceramic. Generally, a "high melting point metal" is a metal, or metal alloy, that has a melting point that is higher than a firing temperature of the blank 102 (or any temperature at which the blank 102 will be fired during processing of the dental blank assembly 100 or formation of a dental appliance), and that is higher than the softening temperature of the bonding composition 108, or at least an initial softening temperature of the bonding composition 108, otherwise referred to as the "bonding temperature" of the bonding composition 108, i.e., the temperature at which the bonding composition 108 is used to bond the blank 102 and the support 104. Particularly, a high melting point metal is a metal that has a melting point that is higher than any processing temperature to which the dental blank assembly 100 will be exposed. In embodiments in which the other components (e.g., the blank 102 and the bonding composition 108, if employed) are generally low-melting point materials (e.g., glasses or glass-ceramics), the metal or metal alloy of the support 104 can have a melting point that is higher than softening temperatures of the other components of the dental blank assembly 100.

In some embodiments, a high melting point metal is a metal having a melting temperature (e.g., softening temperature) greater than about 600° C., in some embodiments, at greater than about 750° C., in some embodiments, greater than about 800° C., in some embodiments, greater than about 950° C., in some embodiments, greater than about 1000° C., in some embodiments, greater than about 1100° C., and in some embodiments, greater than about 1200° C.

Examples of metals or metal alloys that can be employed in the support 104 include, but are not limited to, cobalt chromium, nickel chromium, gold, silver palladium, titanium, other suitable metals or metal alloys, and combinations thereof. Metal alloys having high melting points are used in the dental industry for the fabrication of restorations and restoration components, e.g. porcelain fused to metal crowns. These alloys may be precious metal alloys, or they may be non-precious metal alloys, which are more economical for use as the support 104. Such alloys can be casted into desired support (e.g., mandrel) shapes using investment casting and casting furnaces. Many of the alloys exhibit excellent adhesion to ceramic materials. For the non-precious alloys, such as cobalt-chrome and nickel-chrome alloys, Coefficients of Thermal Expansions (CTEs) generally range from 14-16 ppm, and melting ranges are generally 1200-1420° C. Such alloys are available from multiple suppliers, for example, from Bego USA (Lincoln, R.I.) under the trade names Wirobond, Wirocer, Wiron. Other suppliers include Jensen Dental (New Haven, Conn.), and Ivoclar (Liechtenstein).

Examples of ceramics that can be employed in the support 104 include, but are not limited to, zirconia ($ZrO_2$), alumina ($Al_2O_3$), spinel ($MgAl_2O_4$), leucite (e.g., chemically-derived, such as that described in U.S. Pat. No. 5,622,551), and combinations thereof.

As shown in FIGS. 1 and 2, the support 104 can include a shaft 116 having a longitudinal axis. In the embodiment of FIGS. 1-2, the shaft 116 has an overall cylindrical shape, although other shapes are also possible. For example, the shaft 116 could have a hexagonal shape or an octagonal shape in reference planes perpendicular to its central, longitudinal axis. In general, the support 104 can be shaped and dimensioned to facilitate the dental blank assembly 100 being inserted and reliably held by machining equipment, such as a milling machine. For example, in some embodiments, as shown in FIGS. 1 and 2, an outer end of the shaft 116 can be chamfered to facilitate insertion of the dental blank assembly 100 into a collet or a chuck of machining equipment, such as a milling machine.

As shown, in some embodiments, the support 104 can also include a flange 118 that is connected to an end of the shaft 116 that is opposite the chamfered end. The flange 118 as shown in the drawings also has a cylindrical shape, but has a diameter somewhat larger than the diameter of the shaft 116. In some embodiments, as shown, the central axis of the flange 118 can be collinear with the central axis of the shaft 116, and can presents a flat, outwardly facing bonding surface 120.

However, the flange 118 may have shapes other than cylindrical. For example, the flange 118 may have an overall square, hexagonal or octagonal shape in reference planes perpendicular to its central axis. Moreover, the central axis of the flange 118 may be laterally offset from the central axis of the shaft 116, if desired.

In some embodiments, as shown in FIG. 1, the flange 118 can also includes a notch 122 for registering or indexing the dental blank assembly 100 with respect to machining equipment, for example, for receiving an indexing pin of a milling machine. As shown in the FIGS. 1 and 2, the notch 122 can extend along the outer cylindrical wall of the flange 118, and can extend inwardly toward the central axis of the flange 118. Optionally, but not necessarily, the notch 122 can have a curved inner wall such that the notch 122 presents an overall, generally "U"-shaped configuration when looking in a direction along the central axis of the shaft 116.

In some embodiments, the support 104 may also have other features that align or enhance the coupling between machining equipment and the dental blank assembly 100. For example, the shaft 116 may have a recess or a groove that extends about its circumference to receive a setscrew or other structure of a collet or chuck. Other types of alignment or coupling-enhancing features are also possible, depending on the type of machine(s) selected.

Optionally, all or a portion of the outer cylindrical wall of the flange 118 can provide a calibration surface for use during the machining process (e.g., milling) to establish tool wear. Although the calibration surface in this embodiment has the shape of a cylinder or partial cylinder, other shapes are also possible. The calibration surface may be located next to the notch 122 or alternatively may be located on the peripheral wall in an area opposite the notch 122 relative to the central axis of the flange 118.

If a calibration surface is employed, the calibration surface can be manufactured to be located a precise distance, within very precise dimensional tolerances, from the central axis of the flange 118. For example, in some embodiments, the dimensional tolerance can be plus or minus 0.1 mm, in some embodiments, plus or minus 0.05 mm, and in some embodiments, plus or minus 0.01 mm.

The calibration surface can be used by a machine (e.g., a mill), typically before the machining process begins, as a reference surface to accurately determine the overall dimension (such as the length) of the machining tool (e.g., milling too). As an example, the machine may rotate the tool while slowly moving the tool toward the calibration surface. The machine can have a speed sensor for detecting the rotational speed of the tool and a positional sensor for tracking the axial position of the tool. The rotational speed of the tool slightly decreases as soon as the tool contacts the calibration surface. The machine can be programmed to determine the overall length of the tool and compensate for tool wear by determining the axial position of the tool (i.e., the distance from the central axis of the flange 118) in relation to the calibration surface as soon as a decrease in the rotational speed is detected. Other methods to use the calibration surface as a reference surface are also possible, such as methods that employ laser sighting techniques.

The blank 102 can include any three-dimensional or cross-sectional shape desired, which can be determined at least partially by the type of machining to be performed on the blank 102, and/or the type of material forming the blank 102. By way of example only, the blank 102 of FIGS. 1 and 2 has a generally cuboid shape, with somewhat rounded corners; however, other shapes are possible, such as cylindrical, pyramidal, conical, frusto-pyramidal, frusto-conical, polyhedral, parallelipipedal, other suitable shapes, or combinations thereof.

In addition, in some embodiments, the blank 102 can have a shape in reference planes perpendicular to its central axis that is rectangular, square, hexagonal or other types of polygons or non-polygons including oval. In some embodiments, as shown in FIGS. 1 and 2, the central axis of the blank 102 can be collinear with the central axis of the support 104. By way of example only, the blank 102 of FIGS. 1 and 2 has cross-sectional dimension (e.g., a diameter, if circular in cross-section) that is larger than the cross-sectional dimension (e.g., diameter) of the flange 118 of the support 104, but in some embodiments, the blank 102 can have a cross-sectional dimension that is smaller than a cross-sectional dimension of the flange 118 of the support 104. See, for example, FIGS. 4 and 5, which are described below.

The blank 102 can be formed of a variety of materials that are generally classified as a "ceramic," including, but not limited to, one or more of glasses, glass-ceramics, porcelains, ceramics, and combinations thereof. In some embodiments, the blank 102 and the support 104 are separately formed (i.e., not formed of a unitary or integral construction), and in some embodiments, are formed of different materials. In some embodiments, the blank 102 and the support 104 are formed of the same material, and can be integrally formed, or formed of a unitary construction.

In some embodiments, employing a support 104 and a blank 102 that are formed independently of one another (i.e., "separately formed") can provide the following advantages or benefits: (i) the support 104 can be dimensionally stable, irrespective of the blank 102 and further processing of the blank 102 that may be necessary, so that the support 104 can fit repeatedly and reliably into a machine (e.g., a dental mill); (ii) the blank 102 and the support 104 can be conveniently and separately prepared and later joined (or one of the blank 102 and the support 104 can be formed simultaneously with coupling the blank 102 and the support 104 together), such that the individual needs of each of the blank 102 and the support 104 can be met without consideration for the other until the blank 102 and the support 104 need to be joined together (e.g., the support 104 may need to be shaped within precise tolerances to repeatedly and reliably fit in a desired machine, and the blank 102 needs to be adapted for processing into a dental appliance); (iii) the support 104 can be detached, cleaned and reused after the blank 102 has been formed into the desired dental appliance; (iv) the support 104 can be formed of a less-expensive material than that of the blank 102 (e.g., glass and glass-ceramic materials may not make economically sensible choices for the support 104); and (v) some glasses and/or glass-ceramics that may make excellent blank materials may be too brittle to use as the support 104, because they may not be able to withstand the forces necessary to securely hold (e.g., by a screw) the support 104 in a machine (e.g., in a collet or chuck). The above potential benefits also apply when the blank 102 and the support 104 are formed of different materials.

Examples of glasses that can be employed in the blank 102 of the present disclosure include, but are not limited to, silica, borosilicate glass, sodium oxide, potassium oxide, calcium oxide, flint glass, soda-lime glass, other suitable glass components, or combinations thereof.

Examples of glass-ceramics that can be employed in the blank 102 of the present disclosure include, but are not limited to, lithium disilicate, leucite-reinforced glass-ceramics, and combinations thereof. Other examples of suitable glass-ceramic materials that can be employed include, but are not limited to, Vita Mark II (available from Vita Zahnfabrik, Germany or Vident, USA), Empress CAD (available from Ivoclar Vivadent, Lichtenstein), Paradigm C (available from 3M ESPE, Seefeld, Germany), E-Max CAD (Ivoclar Vivadent), other suitable glass-ceramic materials, or combinations thereof.

Examples of porcelains that can be employed in the blank 102 of the present disclosure include, but are not limited to, feldspathic porcelains.

Examples of ceramics that can be employed in the blank 102 of the present disclosure include, but are not limited to, zirconia ($ZrO_2$), alumina ($Al_2O_3$), spinel ($MgAl_2O_4$), leucite (e.g., chemically-derived, such as that described in U.S. Pat. No. 5,622,551), and combinations thereof. In some embodiments, a fully sintered or fully densified ceramic can be employed such that the blank 102 does not undergo significant shrinkage during processing that may compromise the attachment of the blank 102 with the support 104 and/or the bonding composition 108.

The bonding composition 108 can be used to bond the blank 102 and the support 104 together, and can enhance the bond and connection between the blank 102 and the support 104. Specifically, the bonding composition 108 can be positioned to bond together the support bonding surface 120 and a bonding surface 130 of the blank 102. As shown in FIG. 2, in some embodiments, the bonding composition 108 can extend along entire interfacial area between the bonding surfaces 120 and 130. In other embodiments, the bonding composition 108 may not extend along the entire interfacial area between the bonding surfaces 120 and 130.

Using a bonding composition can be beneficial to increase the bonding strength between the respective surfaces of the blank 102 and the support 104. Without the bonding composition 108, in some embodiments, it might happen that the individual parts do not adhere sufficiently together. This, however, can also depend on the geometry of the parts to be adhered together.

Using a bonding composition can also be beneficial in that it helps improving the fit of the blank 102 and the support 104, e.g. by filling small cavities or recesses in the bonding surfaces 120 and 130. In addition, use of the bonding composition 108 can allow for more facile methods of making the dental blank assembly 100, for example, rather than requiring any specific molding steps to join the blank 102 directly to the support 104. An example of a dental blank assembly formed by directly bonding the blank and the support is described below with reference to FIG. 3.

In some embodiments, the bonding composition 108 which can be used for bonding the blank 102 and the support 104 includes water, a glass and/or glass ceramic material, and optionally a rheological modifier.

In some embodiments, the bonding composition 108 may comprise a rheological modifier. In such embodiments, the rheological modifier may have a molecular weight above about 500,000. The bonding composition 108 may also comprise polyethylene glycol, typically with a molecular weight below about 10,000.

According to one embodiment, the bonding composition 108 can be characterized by one or more of the following features:

Viscosity of liquid without glass and/or glass ceramic material: being in the range of about 10 mPas to about 1,000 mPas or being in the range of about 20 mPas to about 500 mPas, or being in the range of about 30 mPas to about 100 mPas measured at 23° C. with a shear rate of 50 $s^{-1}$ (measured with a viscosimeter MCR301 (Anton Paar Comp.), cone plate geometry, diameter 25 mm, temperature of 23° C., shear rates d(gamma)/dt of 50 $s^{-1}$).

Viscosity of the bonding composition 108 (including glass and/or glass ceramic material): being in the range of about 500 to about 20,000 mPas, or about 1000 to about 10,000 mPas or about 1500 to about 5000 mPas.

If desired, the viscosity measurement can be done a follows: A viscosimeter MCR301 (from Anton Paar Comp.) can be used. A portion of the liquid/powder composition is placed between two steel discs with a diameter of 8 mm and a gap of 1 mm at a temperature of 23° C. The gap is filled completely with the liquid/powder composition. Excess liquid/powder composition is removed. To avoid an undesired drying of the slurry during the measurement a ribbon of wetted paper tissue is laid around the discs in order to raise the humidity. The shear rate between the rotating discs d(gamma)/dt is set constantly to 50 $s^{-1}$. The measurement is done 500 s after starting the shearing process of the composition.

In some embodiments, the bonding composition 108 can be combusted without leaving organic residues, if heated up to a temperature of about 750° C. for about 1 min. at ambient pressure (e.g. 1013 mbar). That is, in some embodiments, the content of organic components (containing carbon) in the bonding composition 108 can be below about 7 wt.-%, in some embodiments, below about 3 wt.-%, and in some embodiments, below about 2 wt.-% with respect to the total weight of the bonding composition 108.

The term "can be combusted without leaving organic residues" means that if about 200 mg of the composition is heated up to a temperature of about 750° C. for about 1 min. at ambient pressure, no visible (visible with the human eye) deposits can be found. That is, the composition either evaporates or can be burnt producing only gaseous components including carbon oxide and water. Except for the glass and/or glass ceramic material being present in the composition essentially no further components are left. This can be determined, if desired, e.g. by visually (with the human eye only) inspecting a final dental restoration obtained after a firing step. A grayish appearance of the dental restoration can be an indicator for a dental composition not fulfilling the above mentioned feature. For example, using a glycerol containing composition typically leads to a dental restoration having a grayish appearance, something which is typically not desirable.

In some embodiments, a metal support can be cast and/or machined to a desired three-dimensional shape, or otherwise formed according to known metal processing methods. In some embodiments, an existing support (e.g., a mandrel for a dental milling machine) can be digitally scanned to obtain a digital surface representation of the desired three-dimensional shape. Then, that digital surface representation can be used to machine (e.g., using CAD/CAM software) the desired support shape out of a desired block of material (e.g., a ceramic dental mill blank, such as a LAVA™ zirconia mill blank, available from 3M ESPE, Seefeld, Germany), factoring in a shrinkage parameter if a ceramic (e.g., zirconia) is employed, such that the resulting support 104 is the proper size after sintering. If the support 104 is formed of a ceramic material, the machined support 104 can then be fully sintered according to the ceramic manufacturer's specifications to achieve a ceramic support that has been sintered to its final or full density. Such sintering can be done, for example, is a LAVA™ furnace available from 3M ESPE.

In embodiments employing a bonding composition 108, the blank 102 can be any commercially available blank that meets the specifications of the present disclosure (e.g., has the proper softening temperature and coefficient of thermal expansion (CTE) for use with the desired support and bonding composition 108, etc.). Otherwise, the blank 102 formed of the desired material can be formed to any desired shape (e.g., block-like, i.e., parallelipipedal) by conventional methods, such as molding, machining, casting, other suitable methods, or combinations thereof.

The blank 102 and the support 104, thus formed, can then be coupled together using the bonding composition 108. For example, the bonding composition 108 can be applied (e.g., coated, painted, brushed, or the like) onto the bonding surface 120 of the support 104 (or a portion thereof) and/or the bonding surface 130 of the blank 102 (or a portion thereof). In some embodiments, the bonding composition 108 can be liberally applied. The support 104 and the blank 102 can then be pressed together, for example, manually using finger pressure, or using a machine or clamp. The assembly can then be heated (e.g., fired) to set, fire, crystallize, or the like, the bonding composition 108. The heating regime can be according to the manufacturer's specifications of the bonding composition 108, and/or can generally include a temperature profile that begins at a temperature lower than the softening temperature of the bonding composition 108 and is gradually increased to a temperature above the softening temperature of the bonding composition 108. By way of example only, in some embodiments, the temperature profile can begin at a temperature of at least 400° C., can be ramped at 30-50° C./min. to a temperature of at least about 600° C., 850° C., 900° C., or another suitable temperature above the softening temperature of the bonding composition 108.

The resulting dental blank assembly 100 can then be cooled, thus producing the dental blank assembly 100 comprising the blank 102 and the support 104 coupled together with the bonding composition 108.

As described above, the components of the dental blank assemblies of the present disclosure need to be coupled together with sufficient structural integrity and dimensional stability that allows for downstream processing, such as machining (e.g., milling, grinding, etc.) and handling As further described above, the softening temperature or range of temperatures of the various components of the dental blank assemblies of the present disclosure need to relate to one another in a particular way to ensure operability and usability of the dental blank assembly 100 as intended (e.g., in downstream heating steps, including firing, glazing, etc.). In general, the softening temperature of the support 104 needs to be high enough to withstand any temperature to which the dental blank assembly 100 will be exposed, both in forming the dental blank assembly 100 (e.g., a bonding temperature necessary to bond the blank 102 and the support 104 with the bonding composition 108), and in any downstream heating steps, such as firing, glazing, fusing additional layers of the dental appliance to the blank 102, etc. For example, in some embodiments, the blank 102 can be milled to form an outer layer, the outer layer can be filled with an additional ceramic-based material (e.g., ceramic, glass, glass-ceramic, and/or porcelain), and the two layers can be fired to fuse or bond the two layers together, and to dry and/or at least partially crystallize one or more of the layers. In such embodiments, the support 104 would generally need to withstand the temperatures at which the additional layer of the dental appliance is formed. In addition, in such embodiments, the blank 102 may further crystallize or densify, but generally retains its shape, size and aspect ratio, such that the attachment of the blank 102 with the support 104 and/or the bonding composition 108.

That is, the support 104 should generally have a softening temperature that is high enough that the support 104 does not undergo an expansion or contraction of the bulk material which would cause unexpected stress to form at the interface between the support 104 and the bonding composition 108 and/or the interface between the support 104 and the blank 102. In addition, the softening temperature of the support 104 is generally high enough to avoid any irreversible changes to the support 104 during any processing steps, e.g., firing, that might affect the fit of the support 104 into a machine (e.g., a milling machine).

In addition, the softening temperature of the support 104 can be higher than the softening temperature of the blank 102, although, the softening temperature of the blank 102 also needs to be high enough to withstand any temperature to which the dental blank assembly 100 will be exposed, both in forming the dental blank assembly 100 (e.g., a bonding temperature necessary to bond the blank 102 and the support 104 with the bonding composition 108) and in any downstream heating steps. As a result, the softening temperature of the support 104 and the softening temperature of the blank 102 are generally higher than the softening temperature of the bonding composition 108 (e.g., the bonding temperature of the bonding composition 108), higher than the bonding temperature at which the bonding composition 108 is used to bond the blank 102 and the support 104, higher than any firing temperatures of the blank 102, higher than any glazing temperatures, and higher than any temperatures necessary to fire, fuse, dry and/or crystallize additional ceramic-based layers of a dental appliance formed on or in the blank 102.

In embodiments in which the bonding composition 108 is employed to couple the blank 102 and the support 104, the bonding temperature at which the blank 102 is coupled to the support 104 is generally higher than the softening temperature of the bonding composition 108 (or at least an initial softening temperature of the bonding composition 108), such that the bonding composition 108 is in its softened, molten or liquid state to bond the blank 102 and the support 104, and then is allowed to cool, dry and/or crystallize to bond the blank 102 and the support 104 together.

In some embodiments, the bonding composition 108 can change after various heating steps, such that the softening temperature of the bonding composition 108 can increase, at least with a first heating step. In such embodiments, the known softening temperature of a bonding composition 108 can be used to bond the blank 102 and the support 104, but the softening temperature of the bonding composition 108 may then increase as a result of such heating steps, similar to an annealing process. In such embodiments, subsequent firing and/or glazing temperatures of the blank 102 may actually occur at temperatures higher than the softening temperature used in the first softening step to bond the blank 102 and the support 104, without destruction (e.g., softening, deforming, etc.) of the bonding composition 108. Such an embodiment is exemplified in Working Examples 1 and 2.

Similarly, the crystalline structure of any of the materials used as the blank 102 or the support 104 can also change as a result of heating, such that the material properties (e.g., softening temperature) can change, depending on the heat history of the material. For example, a lithium silicate may be used as the blank 102 and can be machined when in a precursor state (e.g., lithium silicate, lithium metasilicate) and then fired to change or increase the crystalline structure (e.g., to become a lithium disilicate), and the resulting material may be harder, tougher, etc. than the precursor state, such that the resulting material is suitable as a dental appliance.

As a result, in some embodiments, the order of softening temperatures, from lowest to highest, can be as follows: (1) blank 102 firing and/or glazing, or firing or fusing of additional dental appliance layers; (2) bonding temperature used to originally soften the bonding composition 108 to couple the blank 102 and the support 104; (3) the softening temperature of the blank 102; and (4) the softening temperature of the support 104. As described above, the softening temperature of the bonding composition 108 can change as a response to being exposed to higher temperatures (e.g., after the first softening step used to bond the blank 102 and the support 104), but generally, at any given point in time, the softening temperature of the bonding composition 108 may be between (1) the temperatures at which the blank 102 or additional layers of the dental appliance are fired, fused or glazed, and (2) the softening temperatures of the blank 102 and the support 104 (e.g., such that the blank 102 and the support 104 can withstand the bonding process).

Table 2 lists several exemplary materials that can be employed in the dental blank assembly 100 of the present disclosure as either the blank 102, the support 104, or the bonding composition 108, if employed, along with some material properties for those materials.

TABLE 2

Material properties of various materials that can be employed in the dental blank assemblies of the present disclosure.

| Material | Softening temp (° C.) | CTE (ppm) | Flexural Strength (MPa) |
|---|---|---|---|
| Zirconia | 1500 | 10-10.8 | 900-1200 |
| Lithium disilicate (E MAX CAD[1]) | 850-900 | 10.5 | 360 |
| LAVA ™ ceram porcelain | 820 | 10 | 95 |
| Feldspathic ceramic (VITA VM9[2]) | 670 | 8.8-9.2 | 100 |
| Feldspathic porcelain (VITA Mk II[3]) | 780 | 9.4 | 113 |
| Alumina | 1750 | 8.2 | 379 |
| Leucite reinforced ceramic[4] | Varies[5] | | |
| Non-precious metal dental alloys | Ranges from 1200-1420 | Ranges from 14-16 | |
| Glass solder | Various | | |

[1]available from Ivoclar Vivadent, Amherst, NY
[2]available from Vident, Germany
[3]available from Vident, Germany
[4]Leucite-reinforced ceramics and metals can be used together, since each can have a CTE of approximately 15
[5]Depends on leucite content and heat history.

In some embodiments, it can be important to match the coefficient of thermal expansion (CTE) of several or all of the components of the dental blank assembly 100. Otherwise, in some cases, the blank 102, the support 104 and/or the bonding composition 108 will not be bonded correctly during firing which might lead to failure of the dental blank assembly 100. In some embodiments, glass itself (e.g., including some of the formulations listed above) may match that of zirconia. In some embodiments, for example, when the support 104 comprises a metal, which tends to have a higher CTE, a crystalline material (e.g., leucite) may need to be added to the glass forming the blank 102 or bonding composition 108. Adding leucite to glass can raise the CTE of the glass, and can also improve the mechanical strength of the glass, but crystal materials other than leucite can also be used. The amount of leucite (or other crystal phase) to be added to the glass can depend on the material makeup of the support 104 to which the blank 102 (and/or bonding composition 108) will be coupled, because different metals and alloys have different CTEs. Alumina has a lower CTE compared to zirconia so the glass can be adapted in its composition to reach this lower CTE (e.g. Vita VM7 (VM9 can be used for zirconia, for example), Vita Zahnfabrik, Germany or Vident, USA). Table 3 lists exemplary pairings of support materials, blank materials, and bonding compositions of the present disclosure. The bonding compositions 108 are shown by way of example only; however, it should be understood that in some embodiments, a bonding composition 108 is not necessary, because the blank 102 and support 104 can be direct bonded or fused together without a bonding composition 108. Table 3 is only intended to be illustrative and not limiting:

TABLE 3

Exemplary pairings of blank materials, support materials and bonding compositions

| Support materials | Blank materials | Bonding compositions (if employed) |
|---|---|---|
| Zirconia[1] | Lithium disilicate[2] | Feldspathic porcelain[3] |
| Zirconia[1] | Feldspathic porcelain[4] | Feldspathic porcelain[5] |
| Zirconia[1] | Glass (e.g., SiO$_2$ with Al$_2$O$_3$, K$_2$O, Na$_2$O, etc.) | Glass solder (e.g., SiO$_2$ with Al$_2$O$_3$, K$_2$O, Na$_2$O, etc.) |
| Alumina[6] | Glass (e.g., SiO$_2$ with Al$_2$O$_3$, K$_2$O, Na$_2$O, etc.); or Glass ceramic[7] | Glass (e.g., SiO$_2$ with Al$_2$O$_3$, K$_2$O, Na$_2$O, etc.) |
| Alumina[6] | Alumina[6] | Glass ceramic[7] |
| High Melting Temperature Dental Metal Alloy[8] | Leucite-reinforced glass-ceramic[9] | Feldspathic porcelain[10] |
| Metal | glass ceramic: glass fraction (e.g., SiO$_2$ with Al$_2$O$_3$, K$_2$O, Na$_2$O, etc.) and crystalline fraction (e.g. leucite)[11] | glass ceramic: glass fraction (e.g., SiO$_2$ with Al$_2$O$_3$, K$_2$O, Na$_2$O, etc.) and crystalline fraction (e.g. leucite) |

[1]e.g., from 3M ESPE, Seefeld, Germany
[2]e.g., E MAX CAD, available from Ivoclar Vivadent, Amherst, NY
[3]e.g., LAVA ™ Ceram Shoulder Porcelain, available from 3M ESPE
[4]e.g., VITA Mk II, available from Vita Zahnfabrik, Germany or Vident, USA TABLE 3-continued Exemplary pairings of blank materials, support materials and bonding compositions

| Support materials | Blank materials | Bonding compositions (if employed) |
|---|---|---|

[5]e.g., VITA VM9, available from Vita Zahnfabrik, Germany or Vident, USA
[6]e.g., VITA alumina, available from Vita Zahnfabrik, Germany or Vident, USA
[7]e.g., VITA VM7, available from Vita Zahnfabrik, Germany or Vident, USA
[8]e.g., Begostar Wirobond LFC, available from Bego USA, Lincoln, RI
[9]e.g., EMPRESS CAD, available from Ivoclar Vivadent
[10]The CTE of feldspathic porcelains can be controlled/dictated by the leucite content, such that the CTE can be increased by increasing the leucite content; leucite content can be a result of heat history; one example is Finesse Porcelain, available from Dentsply, York, PA
[11]e.g., VITA VM13, which has a CTE of ~13, available from Vita Zahnfabrik, Germany or Vident, USA In some embodiments, matching CTEs means that the CTE of any of the components of the dental blank assembly 100 differ by no more than 2.0, in some embodiments, by no more than 1.5, in some embodiments, by no more than 1.0, and in some embodiments, by no more than 0.5. For example, in some embodiments, the CTE of the blank 102 differs from the support 104 and the bonding composition 108 (if employed), and vice versa, by no more than 2.0, 1.5, 1.0, or 0.5. For example, in some embodiments, the blank 102 can have a first CTE, the support 104 can have a second CTE, and the bonding composition, if employed, can have a third CTE, and the first, second, and third CTEs each differ from the other CTEs by no more than 2.0, 1.5, 1.0, or 0.5.

FIG. 3 illustrates another dental blank assembly 200 according to the present disclosure, wherein like numerals represent like elements. The dental blank assembly 200 shares many of the same elements and features described above with reference to the illustrated embodiment of FIGS. 1 and 2. Accordingly, elements and features corresponding to elements and features in the illustrated embodiment of FIG. 3 are provided with the same reference numerals in the 200 series. Reference is made to the description above accompanying FIGS. 1 and 2 for a more complete description of the features and elements (and alternatives to such features and elements) of the embodiment illustrated in FIG. 3.

A shown in FIG. 3, the dental blank assembly 200 includes a blank 202 directly coupled to a support 204. FIG. 3 shows a cross-section through the dental blank assembly 200 in which it is clear that the blank 202 and the support 204 are directly bonded together without the use of a bonding composition. For example, the support 204 is illustrated as having a bonding surface 220 that is directly bonded to a bonding surface 230 of the blank 202. Thus, FIG. 3 illustrates an example of a dental blank assembly according to the present disclosure wherein the means for coupling includes direct bonding of the blank 202 and the support 204. The various materials described above with reference to FIGS. 1 and 2 for the blank 102 and the support 104 can also be used for the blank 202 and the support 204 of the dental blank assembly 200.

In some embodiments, the dental blank assembly 200 can be formed using wax-investment molding processes. In such processes, the support 204 can be formed by first creating a wax design or pattern of the desired three-dimensional support shape, for example, via milling and/or rapid prototyping. Such a support shape can be designed to fit a known dental milling system, for example, using CAD/CAM software. In some embodiments, the design can include various mechanical inter-engaging structures, such that the resulting blank 202 and support 204 are also mechanically inter-engaged, such as the embodiment shown in FIGS. 4 and 5 and described below. Other acceptable mechanical interlock designs are described in U.S. Pat. No. 6,669,875, which is incorporated herein by reference, and could further include ribs or other roughening textures to increase the inter-engagement or interlock between the blank and support.

The wax replica of the desired three-dimensional support shape can then be invested in a casting investment material, such as a dental casting investment (e.g., Microstar HS Investment (Jensen Dental, New Haven, Conn.)). After the investment has set, the wax replica can be burned out, and the investment can be loaded with the desired support material (e.g., a metal alloy). The support can then be allowed to cool before breaking out and devesting, thus producing the support 204. In some embodiments, the bonding surface 220 of the support 204 can be further processed (e.g., sandblasted or otherwise textured) to increase adhesion with the bonding surface 230 of the blank 202.

A wax replica of the desired three-dimensional shape of the blank 202 can then be provided, for example, by milling, molding, or rapid-prototyping, and can be created directly on the bonding surface 220 of the support 204 to form an intermediate assembly. The intermediate assembly can then be invested in an appropriate investment material, such as the Microstar HS Investment. The wax replica of the blank 202 can then be burned out, and the desired blank material can be loaded into the investment cast. In some embodiments, the desired blank material can be pressed into the cast with a plunger, which can be pre-heated. Such pressing can be done in a pressing oven, for example.

Other details of an exemplary direct bonding process for forming the dental blank assembly 200 are described in Prophetic Example 3.

FIGS. 4 and 5 illustrate another dental blank assembly 300 according to the present disclosure, wherein like numerals represent like elements. The dental blank assembly 300 shares many of the same elements and features described above with reference to the illustrated embodiment of FIGS. 1-3. Accordingly, elements and features corresponding to elements and features in the illustrated embodiment of FIGS. 4 and 5 are provided with the same reference numerals in the 300 series. Reference is made to the description above accompanying FIGS. 1-3 for a more complete description of the features and elements (and alternatives to such features and elements) of the embodiment illustrated in FIGS. 4 and 5.

As shown in FIGS. 4 and 5, the dental blank assembly 300 includes a blank 302 and a support 304 adapted to be coupled together at least partially by a mechanical inter-engagement or interlock. In addition, the blank 302 and the support 304 can be directly bonded, such as described above with respect to the dental blank assembly 200 of FIG. 3, and/or bonded with a bonding composition, such as described above with respect to the dental blank assembly 100 of FIGS. 1 and 2, and further described below.

As shown in FIGS. 4 and 5, the support 304 can include a shaft 316 having a longitudinal axis, which can include all the features described above with respect to the shaft 116 of FIGS. 1 and 2. Similarly, the support 304 can include a flange 318, a bonding surface 320, and a notch 322, each of which can include all the features described above with respect to the flange 118, the bonding surface 120, and the notch 122 of FIGS. 1 and 2.

As part of the mechanical inter-engagement, the support 304 also includes a recess 324 that is located in the flange 318, and/or is formed in the bonding surface 320 of the support 304. In the illustrated embodiment, the recess 324 has an overall generally cylindrical shape with a central axis that is collinear with the central axis of the flange 318 and the central axis of the shaft 316. As a consequence, the recess 324 is located in this embodiment in the center of the bonding surface 320. The inner end of the recess 324 has a generally dome-shaped configuration.

However, the recess 324 may alternatively have other shapes and be located in offset relation to the central axis of the flange 318. For example, the recess 324 may have a square, rectangular, oval or other shape in reference planes perpendicular to the central axis of the flange 318. Optionally, the recess 324 may have a length sufficient to extend into the adjacent end portion of the shaft 316.

As shown in FIGS. 4 and 5, the blank 302 includes a main body 326 as well as a projection 328 that is connected to the main body 326. In some embodiments, the body 326 and the projection 328 can be integrally formed together and form part of a single, unitary body; however, this need not be the case. For example, in some embodiments, the projection 328 can be coupled to the blank 302 using a bonding composition according to the present disclosure. In the embodiment shown in FIGS. 4 and 5, the body 326 has an overall cylindrical shape, although other shapes are also possible. In addition, the projection 328 is shaped and dimensioned to be received in the recess 324 of the support 304, but the projection 328 and the recess 324 can have other shapes, as long as their respective shapes accommodate one another and provide for a mechanical inter-engagement.

In some embodiments, the blank 302 may have a shape in reference planes perpendicular to its central axis that is rectangular, square, hexagonal or other types of polygons or non-polygons including oval. In some embodiments, as shown in FIGS. 4 and 5, the central axis of the body 326 is collinear with the central axis of the projection 328. The body 326 as shown has a cross-sectional dimension (e.g., diameter) that is smaller than the cross-sectional dimension (e.g., diameter) of the flange 318 of the support 304, but as another option, could have a cross-sectional dimension or overall shape that is larger than the cross-sectional dimension or overall shape of the support 304 or a portion thereof, such as the flange 318.

In some embodiments, the projection 328 can have a cross-sectional configuration in reference planes perpendicular to its central axis that is closely complementary to the cross-sectional configuration of the recess 324. As a consequence, the projection 328 can matingly fit within the recess 324 when the support 304 and the blank 302 are assembled together. In some embodiments, the central axis of the body 326 and the projection 328 are collinear with the central axis of the flange 318 and the shaft 316 when the support 304 and the blank 302 are assembled, as shown in FIGS. 4 and 5.

In some embodiments, the recess 324 can have a length in directions along its central axis that is somewhat longer than the length of the projection 328. As a consequence, when the support 304 and the blank 302 are coupled together, the bonding surface 320 of the support 304 can tightly and intimately contact an annular flat bonding surface 330 of the blank 302 that surrounds the projection 328. The extra depth provided in the recess 324 can ensure that the bonding surfaces 320 and 330 will fully meet even in instances where the length of the projection 328 is somewhat larger than expected.

In some embodiments, the projection 328 and the recess 324 can be configured to provide an interference fit. For example, the cross-sectional configuration of the projection 328 can be slightly larger than the cross-sectional configuration of the recess 324 in reference planes perpendicular to the central axis of the assembly 300 so that an interference fit is presented. In that instance, the projection 328 can be forced under pressure into the recess 324 in order to establish a secure press-fit relationship when the support 304 and the blank 302 are coupled together.

As mentioned above, in some embodiments, a bonding composition can be provided to enhance the bond between the support 304 and the blank 302. In such embodiments, the bonding composition can extend between the entire area of the bonding surfaces 320 and 330, and/or along the interfacing surfaces of the projection 328 and the recess 324 that are in contact with each other.

The dental blank assembly 300 includes the projection 328 on the blank 302 and the recess 324 in the support 304 by way of example only; however, it should be understood that the blank 302 can alternatively, or additionally, include a recess, and the support 304 can alternatively, or additionally, include a mating projection. That is, one of the blank 302 and the support 304 can include the projection 328, and the other of the blank 302 and the support 304 can include the recess 324 that is dimensioned to receive the projection 328. As a result, the mechanical inter-engagement shown in FIGS. 4 and 5 is shown by way of example only, but additional inter-engaging structures can be employed to provide a mechanical means for coupling the blank 302 and the support 304.

Dental blank assemblies of the present disclosure employing such a mechanical inter-engaging structure can have an enhanced resistance to fracture during downstream machining processes, and can be particularly suited to safely resist forces exerted by a machining tool (e.g., a milling tool) in lateral directions so that a dental appliance can be machined to completion without unintentional and undesirable detachment of the support 304 from the blank 302.

The mechanical inter-engaging structures shown in FIGS. 4 and 5, or other suitable and similar inter-engaging structures, can also be employed in the dental blank assemblies of FIGS. 1-3, and need not only be employed in dental blank assemblies having the shapes and/or geometries of the dental blank assembly 300 of FIGS. 4 and 5.

Examples of methods for making a blank and a support having interlocking or inter-engaging features or structures are described in U.S. Pat. Nos. 6,482,284 and 6,669,875, which are incorporated herein by reference.

The dental blank assemblies 100, 200 and 300 are shown to illustrate various features and elements of the present disclosure; however, it should be understood that various features and elements of the dental blank assemblies 100, 200 and 300 can be combined without departing from the spirit and scope of the present disclosure.

One exemplary method of the present disclosure will now be described in greater detail with reference to FIG. 6.

Exemplary Method of the Present Disclosure

FIG. 6 illustrates a method 600 according to one embodiment of the present disclosure, for forming a dental restoration. The method 600 generally includes a first sequence 602 and a second sequence 604. The first sequence 602 and the second sequence 604 can include some temporal overlap, such that at least some of the steps in the first sequence 602 can occur while some of the steps in the second sequence 604 are being performed, or vice versa. In general, the first sequence 602 includes steps that can be performed on the patient, while the second sequence 604 generally refers to steps that include manipulating data, designing digital surface representations, and/or fabricating the dental restoration. Thus, the first sequence 602 generally takes place chairside. The second sequence 604 can also take place chairside (or in a back room or a portion of a dentist's office, which can also generally be referred to as "chairside" or "single-appointment" or "same day" because the steps are being performed while the patient is still at his/her appointment). As described above, in some embodiments, the second sequence 604 can take place partially chairside and partially remotely from the location of the patient. If the remote location is geographically near the location of the patient, however, the entire process can still occur while the patient is at his/her appointment, even if some of the software manipulation and/or fabrication steps are actually performed off-site, or remote from the location of the patient.

In the first sequence 602, a first step 606 of capturing the pre-op condition can be performed, which can include optically scanning a patient's soft tissue and dentition via one or more intraoral digital scans, or optically scanning a model (e.g., a standard model or a model of the patient's intraoral cavity), using the above-described digital workflow techniques. As shown in step 610, the digital data acquired from the scan can then be stored. The digital data files stored in step 610 can then be used, for example, at step 614, to design the outside contour of the restoration and to create a first digital surface representation (e.g., using CAD software). The inside contour of the desired outer layer can also be designed at step 614.

As further shown in FIG. 6, at step 616, a dental blank assembly comprising a blank coupled to a support can be provided. The dental blank assembly configured to withstand downstream firing and machining processes. At step 616, the outside contour of the restoration can then be milled out of the blank which comprises a first material using any standard dental milling fabrication tool. As discussed above, all of the steps 610, 614 and 616 can be performed during or prior to a tooth preparation step 620 (described below), and/or at a dental laboratory, remote from the dentist's office. The dental restoration formed in step 616 is generally referred to herein as a "first article," and the first article can be polished (e.g., while still being coupled to the support). Step 616 can also include providing a first assembly comprising the first article coupled to the support (e.g., mandrel). The first material can have certain structural and/or optical properties. For example, in some embodiments, the first material can be adapted to form an "enamel shell" that will be stronger and/or harder than an inner "dentin-like" layer. In addition, the first material can be enamel-shaded.

As shown in FIG. 6, at step 615, the first article (e.g., the first assembly comprising the first article coupled to the support) can optionally be fired to densify the first article having the desired outer shape.

With continued reference to FIG. 6, at step 617, an outer layer of the restoration can be formed by milling a cavity in the first article (or the fired first article). As described above, in some embodiments, the data regarding the specifics of the outer layer (e.g., internal mammelon structures, if applicable, thickness, etc.) can be included in the first digital surface representation. Because the first article is generally still coupled to the support (e.g., a mandrel or frame, e.g., by a sprue), the cavity can be formed in the first article by remounting the first article in the same tool as that in which the outer shape was formed, or a different tool. As a result, step 617 can further include providing a second assembly comprising the outer layer coupled to the support. The support can facilitate registration of the second article in a fabrication tool, and can assist in indexing or registering the first article with respect to the fabrication tool when the cavity of the outer layer is formed in the first article (described below).

Alternatively, in embodiments in which the cavity will be formed in the same tool (e.g., mill) as the outer shape was formed, the first article can simply remain positioned in the fabrication tool (i.e., still coupled to or including the mandrel, sprue, etc.) after the outer shape is formed. Furthermore, in some embodiments, as described above, the cavity (e.g., internal surface) of the outer layer can be formed at the same time that the outer shape (e.g., external surface) is formed. In such embodiments, steps 616 and 617 can occur simultaneously as one step, and the resulting product can be a first article having the desired outer shape and the cavity. In such embodiments, the "first assembly" comprising the first article having only the desired outer shape coupled to the support may exist only briefly before the cavity is formed and the "second assembly" comprising the outer layer coupled to the support is formed."

The outer layer or "enamel shell" can optionally be stained and/or glazed to achieve a desired outer surface. As shown in FIG. 6, at step 619, the outer layer (e.g., the second assembly comprising the outer layer coupled to the support) can optionally be fired to densify the outer layer or shell. In some embodiments, both the first article (e.g., first assembly) and the outer layer (e.g., second assembly) can be fired, and in some embodiments, only the outer layer (e.g., second assembly) is fired.

At step 618, a second article can then be formed by filling the cavity of the first article with a second material. As a result, step 618 can also include forming a third assembly comprising the second article coupled to the support. At step 621, the second article (e.g., the third assembly comprising the second article coupled to the support) can optionally be fired to densify the second material and/or the first material, or to bond or fuse the first material (e.g., the outer layer) to the second material. Furthermore, as described above, step 618 can actually include multiple layering steps, applying the second material in thin layers. Each layer can be individually fired at step 621.

The second material will form the inner layer of the final dental restoration, and in the exemplary method 600, the second material can have at least one different structural property (e.g., is softer, more shock-aborptive, and/or more resilient than the first material) and at least one different optical property (e.g., the second material can be darker than the first material) than the first material to form a biomimetic, multi-chromatic, multi-layer dental restoration. It can also be important that the outer layer and the inner layer (i.e., formed of the first material and the second material, respectively) have good interfacial bonding, for example, for structural integrity and sufficient biomimetics. In some embodiments of the method 600, step 618 (or step 621) can be the final step, and the resulting product can be an intermediate, all-ceramic, multi-layer dental restoration, capable of being further processed as needed. Such a resulting intermediate can include or be coupled to the support to facilitate downstream processing.

While steps 610, 614, 616, 617, 618 (and optionally, one or more of steps 615, 619 and 621), are being performed, other actions can be taking place at the location of the patient. Alternatively, the following steps can occur after steps 610, 614, 616, 617, 618 (and optionally, one or more of steps 615, 619 and 621) are complete. At step 620, a dental object can be formed, for example, by preparing a tooth to receive the dental restoration by removing carious dental tissue (e.g., hard tissue), by preparing an implant abutment (e.g., by coupling the implant abutment to an implant), according to known methods, or a combination thereof.

At step 626, a "post-prep" digital impression of the dental object can then be obtained, for example, by optically scanning the dental object.

Similar to step 614 above, the digital data files acquired at step 626 can be stored at step 630. Then, at step 634, the inside contours of the dental restoration can be designed, and the second digital surface representation can be formed. Also, at step 634, the first digital surface representation and the second digital surface representation can be merged and registered to form a complete three-dimensional digital representation of the desired dental restoration. In some embodiments, the second article can be considered to include, or be coupled to, a mandrel or holder that facilitates placement of the second article into a fabrication tool, such as a mill. As mentioned above, the second article (e.g., the fired second article) can further include, or be coupled to, a sprue that allows the second article to remain coupled to the support (i.e., forming the third assembly), but from which the final dental restoration will be removed. The support can facilitate registration of the second article in a fabrication tool, and can assist in indexing or registering the second article with respect to the fabrication tool when the inner shape of the dental restoration is formed in the second article (described below). In addition, in some embodiments, at step 634, any manipulation of the three-dimensional digital representation of the desired dental restoration can be performed, and margins can be designed into the model, along with any other necessary finalizing or data enhancement steps.

At step 636, the second article from step 618 (or the fired second article from step 621) can be milled to achieve the desired inside contour of the dental restoration to form the dental restoration having the desired outer shape (e.g., including margin(s)) and the desired inner shape.

Step 616, or the combination of steps 616, 617 and 618 (and optionally, one or more of steps 615, 619 and 621), can generally be referred to as the first fabrication step, or the "outer fabrication step," and step 636 can generally be referred to as the second fabrication step, or the "inner fabrication step," even though the inner fabrication step can include any finalizing that needs to be done with respect to the outer shape of the dental restoration. As a result, the fabrication steps for forming the inner shape of the dental restoration can be separated from and performed subsequently to steps for fabricating the outer shape of the dental restoration (with the exception of margins, or any additional finalizing of the outer shape, which can also be performed at step 636). As mentioned above, steps 616-618 (and optionally, one or more of steps 615, 619 and 621) need not be entirely completed before step 620 begins. Rather, steps 620 and 626 can occur while any of steps 610, 614, 616, 617 and 618 (and optionally, one or more of 615, 619 and 621) are still being performed.

Finally, as shown in FIG. 6, the method can include step 640, in which the completed restoration is placed in the patient's mouth, for example, using any cementation techniques known in the art.

In some embodiments, the method 600 can be described as including a first (or "outer") sequence 642 for creating the outer shape of the desired dental restoration, and a second (or "inner") sequence 644 for creating the inner shape of the desired dental restoration. In some embodiments, the outer sequence 642 can include steps 606, 610, 614, 616, 617 and 618 (and optionally, one or more of steps 615, 619 and 621), and the inner sequence 644 can include steps 620, 626, 630, 634 and 636. At least a portion of the outer sequence 642 can overlap temporally with the inner sequence 644, such that the inner sequence 644 can be initiated before the outer sequence 642 has been fully completed. Furthermore, as described above, the outer sequence 642 can be performed prior to the patient's visit, such that the second article (i.e., the third assembly) is already prepared and ready for the inner sequence 644 to be completed when the patient arrives for his/her appointment. Alternatively, as described above, both the outer sequence 642 and the inner sequence 644 can be completed while the patient is at his/her appointment. In either scenario, the patient can leave the appointment with the desired dental restoration in place in his/her mouth.

Furthermore, in some embodiments, the outer sequence 642 can generally include a first sequence 646 for forming the first article (e.g., the first assembly and/or the second assembly), and a second sequence 648 for forming the second article (e.g., the third assembly). In the first sequence 646, the desired outer shape can be milled into a mill block of a desired first material having a desired structural and/or optical property to form the first article (i.e., step 616 in FIG. 6), the first article can optionally be fired (i.e. step 615), and then a cavity can be milled out of the first article (or fired first article) to form an outer layer of the dental restoration that includes the desired thickness, internal mammelon structure(s), translucency, etc. (i.e., step 617 in FIG. 6). The outer layer can optionally be fired (i.e., step 619). In some embodiments, forming the cavity in the first article (i.e., step 617 in FIG. 6) can be considered to be a part of the first sequence 646, and in some embodiments, forming the cavity can be considered to be a part of the second sequence 646. The second sequence 648 can include forming the second article by filling the cavity in the first article, for example, with a second material having at least one structural and/or optical property that differs from the first material, such that the second article is biomimetic (and, optionally, multi-chromatic), and includes at least two layers. The second article can optionally be fired (i.e., step 621).

As mentioned above, steps 617 and 618 (and optionally, one or both of steps 619 and 621) can be repeated as many times as desired to form a second article having the desired number of layers, the desired level of biomimicry, the desired level of multi-chromaticity, the desired outer shape of the dental restoration, and the inner layer, in which the desired final inner shape of the dental restoration will be formed (i.e., step 636).

The method 600 is shown in FIG. 6 and described above for illustration purposes only, and it should be understood that the methods of the present disclosure are not limited to the specific embodiment shown in FIG. 6 and described above.

The following is a description of various embodiments of the present disclosure.

EMBODIMENTS

Embodiment 1 is a method of making a dental appliance, the method comprising:
  providing a first digital surface representation of a desired outer shape of a dental appliance;
  forming a first article of a first material having the desired outer shape based on the first digital surface representation, the first material comprising at least one of a glass, a glass-ceramic, a porcelain, and a ceramic;
  removing an inner portion of the first article to form an outer layer of the dental appliance comprising a cavity dimensioned to accommodate an inner layer;

forming a second article by filling the cavity of the first article with a second material adapted to form the inner layer, the second material comprising at least one of a glass, a glass-ceramic, a porcelain, and a ceramic; and firing at least one of the first article, the outer layer, and the second article.

Embodiment 2 is the method of embodiment 1, wherein firing at least one of the first article, the outer layer, and the second article includes firing at least one of the first article, the outer layer, and the second article while the first article, the outer layer, or the second article, respectively, is coupled to a support.

Embodiment 3 is the method of embodiment 2, wherein the support is configured to withstand any firing of at least one of the first article, the outer layer, and the second article.

Embodiment 4 is the method of embodiment 2 or 3, wherein the support is formed of at least one of a metal, metal alloy, and a ceramic.

Embodiment 5 is the method of any of embodiments 1-4, wherein the first article forms a portion of a first assembly, the first assembly comprising the first article coupled to a support, and wherein firing the first article includes firing the first assembly.

Embodiment 6 is the method of any of embodiments 1-5, wherein the outer layer forms a portion of a second assembly, the second assembly comprising the outer layer coupled to a support, and wherein firing the outer layer includes firing the second assembly.

Embodiment 7 is the method of any of embodiments 1-6, wherein the second article forms a portion of a third assembly, the third assembly comprising the second article coupled to a support, and wherein firing the second article includes firing the third assembly.

Embodiment 8 is the method of any of embodiments 1-7, further comprising providing a dental blank assembly comprising a blank coupled to a support, the blank being formed of the first material, wherein the first article is formed in the blank of the dental blank assembly.

Embodiment 9 is the method of embodiment 8, wherein the first article, the outer layer, and the second article are each coupled to the support, and wherein firing at least one of the first article, the outer layer and the second article includes firing the support.

Embodiment 10 is the method of embodiment 8 or 9, wherein the dental blank assembly is configured to withstand temperatures necessary to fire at least a portion of the assembly in a downstream firing process.

Embodiment 11 is the method of any of embodiments 8-10, wherein the dental blank assembly is configured to mechanically withstand a downstream machining process.

Embodiment 12 is the method of any of embodiments 8-11, wherein the dental blank assembly further comprises a bonding composition positioned between the blank and the support to couple the blank and the support, the bonding composition having a bonding temperature that is lower than a softening temperature of the blank and that is lower than a softening temperature of the support.

Embodiment 13 is the method of embodiment 12, wherein the support is formed of at least one of a high melting point metal and a ceramic, and wherein a high melting point metal is a metal or metal alloy that has a melting point that is higher than a firing temperature of the blank, and that is higher than the bonding temperature of the bonding composition.

Embodiment 14 is the method of embodiment 12 or 13, wherein the blank has a first coefficient of thermal expansion (CTE), wherein the support has a second CTE, and wherein the bonding composition has a third CTE, wherein the first CTE and the second CTE differ by no more than 2.0, wherein the second CTE and the third CTE differ by no more than 2.0, and wherein the first CTE and the third CTE differ by no more than 2.0.

Embodiment 15 is the method of any of embodiments 8-11, wherein the dental blank assembly further comprises a means for coupling the blank and the support, wherein the means for coupling includes at least one of a mechanical inter-engagement, a direct bond, a bonding composition, and a combination thereof.

Embodiment 16 is the method any of embodiments 8-15, wherein the support is formed of at least one of a metal, metal alloy, and a ceramic.

Embodiment 17 is the method of any of embodiments 8-11, wherein the dental blank assembly is formed of a unitary construction, such that the blank and the support are integrally formed of the same material.

Embodiment 18 is a method of making a multilayer all-ceramic dental appliance, the method comprising:

providing a first digital surface representation of a desired outer shape of a dental appliance;

providing a dental blank assembly comprising a blank coupled to a support, the blank being formed of a first material, the first material comprising at least one of a glass, a glass-ceramic, a porcelain, and a ceramic;

forming a first article of the blank while the blank is coupled to the support, the first article having the desired outer shape based on the first digital surface representation;

providing a first assembly comprising the first article coupled to the support;

removing an inner portion of the first article, while the first article is coupled to the support, to form an outer layer of the dental appliance comprising a cavity dimensioned to accommodate an inner layer;

providing a second assembly comprising the outer layer coupled to the support;

forming a second article by filling the cavity of the outer layer with a second material adapted to form the inner layer, the second material comprising at least one of a glass, a glass-ceramic, a porcelain, and a ceramic;

providing a third assembly comprising the second article coupled to the support; and firing at least one of the first assembly, the second assembly, and the third assembly.

Embodiment 19 is the method of embodiment 18, wherein the first article, the outer layer, and the second article are each coupled to the support, and wherein firing at least one of the first article, the outer layer and the second article includes firing the support.

Embodiment 20 is the method of embodiment 18 or 19, wherein the dental blank assembly is configured to withstand temperatures necessary to fire at least a portion of the assembly in a downstream firing process.

Embodiment 21 is the method of any of embodiments 18-20, wherein the dental blank assembly is configured to mechanically withstand a downstream machining process.

Embodiment 22 is the method of any of embodiments 18-21, wherein the dental blank assembly further comprises a bonding composition positioned between the blank and the support to couple the blank and the support, the bonding composition having a bonding temperature that is lower than a softening temperature of the blank and that is lower than a softening temperature of the support.

Embodiment 23 is the method of embodiment 22, wherein the support is formed of at least one of a high melting point metal and a ceramic, and wherein a high melting point metal is a metal or metal alloy that has a melting point that is higher than a firing temperature of the blank, and that is higher than the bonding temperature of the bonding composition.

Embodiment 24 is the method of embodiment 22 or 23, wherein the blank has a first coefficient of thermal expansion (CTE), wherein the support has a second CTE, and wherein the bonding composition has a third CTE, wherein the first CTE and the second CTE differ by no more than 2.0, wherein the second CTE and the third CTE differ by no more than 2.0, and wherein the first CTE and the third CTE differ by no more than 2.0.

Embodiment 25 is the method of any of embodiments 18-21, wherein the dental blank assembly further comprises a means for coupling the blank and the support, wherein the means for coupling includes at least one of a mechanical inter-engagement, a direct bond, a bonding composition, and a combination thereof.

Embodiment 26 is the method any of embodiments 18-25, wherein the support is formed of at least one of a metal, metal alloy, and a ceramic.

Embodiment 27 is the method of any of embodiments 18-21, wherein the dental blank assembly is formed of a unitary construction, such that the blank and the support are integrally formed of the same material.

Embodiment 28 is the method of any of embodiments 1-27, further comprising:
  providing a dental object having an outer shape comprising the negative of a desired inner shape of the dental appliance;
  acquiring a second digital surface representation of the outer shape of the dental object;
  subtractively forming the desired inner shape in the second article based on the second digital surface representation to form the dental appliance having the desired inner shape and the desired outer shape.

Embodiment 29 is the method of embodiment 28, wherein the dental object includes at least one of a tooth stump, an implant, an implant abutment, a healing cap, and a combination thereof.

Embodiment 30 is the method of embodiment 28 or 29, wherein acquiring a second digital surface representation of the outer shape of the dental object includes optically scanning the dental object.

Embodiment 31 is the method of any of embodiments 28-30, wherein subtractively forming the desired inner shape in the second article includes milling the desired inner shape.

Embodiment 32 is the method of any of embodiments 28-31, wherein at least two of forming a first article, removing an inner portion of the first article, and subtractively forming the desired inner shape in the second article are performed by the same fabrication tool.

Embodiment 33 is the method of any of embodiments 28-32, wherein at least two of forming a first article, removing an inner portion of the first article, and subtractively forming the desired inner shape in the second article occur at different locations from one another.

Embodiment 34 is the method of any of embodiments 28-33, wherein at least one of providing a dental object and acquiring a second digital surface representation occurs during or after at least one of forming a first article, removing an inner portion of the first article, and forming a second article, and wherein subtractively forming the desired inner shape occurs separately from and subsequently to forming a first article of a first material having the desired outer shape.

Embodiment 35 is the method of any of embodiments 1-34, further comprising repeating the removing an inner portion of the first article step and the forming a second article step as many times as desired to form a second article having a desired number of layers and comprising the inner layer.

Embodiment 36 is the method of any of embodiments 1-35, wherein the second material has at least one material property that is different from the first material, such that the dental appliance is biomimetic.

Embodiment 37 is the method of any of embodiments 1-36, wherein the second material has at least one optical property that is different from the first material, such that the dental appliance is also multi-chromatic.

Embodiment 38 is the method of any of embodiments 1-37, further comprising acquiring a third digital surface representation of the second article.

Embodiment 39 is the method of any of embodiments 1-38, further comprising merging the first digital surface representation and the second digital surface representation to form a three-dimensional digital representation of the dental appliance.

Embodiment 40 is the method of any of embodiments 1-39, further comprising designing a three-dimensional digital representation of the dental appliance, wherein designing a three-dimensional digital representation includes merging the first digital surface representation and the second digital surface representation.

The following examples are intended to be illustrative of the present disclosure and not limiting.

EXAMPLES

Preparatory Example 1

Preparation of a Dental Blank Assembly Used in Examples 1 and 2

Support (Mandrel) Fabrication

A commercially available metal mandrel designed to fit into a Cerec 3 milling unit (Sirona, Germany) was scanned with a LAVA™ ST Scanner (3M ESPE). The scan data were used to mill a LAVA™ Zirconia mill blank (3M ESPE) into the same shape as the metal mandrel, factoring in a shrinkage parameter such that the zirconia mandrel was the proper size after sintering. The milled zirconia was fully sintered per manufacturer's instructions in a LAVA™ Furnace 200 (3M ESPE), thus producing a fully sintered zirconia mandrel.

Mill Blank Attachment to the Mandrel

A feldspathic porcelain (Vita Mark II, Shade A3, Vident, Bad Sackingen, Germany) mill blank not having a mandrel was placed on a surface and a slurry of Vita VM9 porcelain (Vident) and LAVA™ Ceram Modeling Liquid (3M ESPE) was liberally painted on both the mill blank and the sintered zirconia mandrel. The mandrel was then pressed onto the blank using finger pressure and the assembly was carefully placed into a furnace (Vita Vacumat 4000T, Vident) and fired using the following temperature profile: 500 deg. C. for 6 min., then ramped at 25 deg. C./minute to 910 deg. C. and held at 910 deg. C. for 3 minutes. The vacuum was on during the heating and released when the temperature reached 910 deg. C. The fired assembly was slow cooled to 600 deg. C. and then cooled to room temperature, thus producing a mill blank attached to a mandrel (dental blank assembly).

Example 1

Chairside Preparation of an all-Ceramic Multi-Chromatic Dental Restoration for a Patient Needing a Full Crown Using a Cerec 3 milling unit, an external shape in the form of an anterior prep was selected from the software library.

Using the same software, an internal cavity was designed to have the same shape as the external surface, but being about 1 mm smaller, thus leaving a 1 mm exterior shell. This design of the outer layer of the restoration was then sent to the milling unit and milled from the dental blank assembly of Preparatory Example 1 to form the outer layer (which includes the desired outer shape and an internal cavity) of the restoration. A sprue was left, attaching the outer layer to the mandrel (thereby forming a "second assembly"). The outer layer and mandrel (i.e., the "second assembly") were removed from the mill.

The hollow interior of the outer layer was then positioned with the open base facing upwards and filled with a slurry of Vita VM9 (enamel shade, Vident) and LAVA™ Ceram Modeling Liquid. The filled outer layer (i.e., the second article), still attached to the mandrel (i.e., the third assembly comprising the second article coupled to the support), was carefully placed into a Vita Vacumat 4000T furnace and subsequently fired using the following temperature profile: 500° C. for 6 min., ramped at 25° C./minute to 910° C. and held at 910° C. for 3 min. The vacuum was on during the heating and released when the temperature reached 910° C. The fired assembly was slow cooled to 600° C., and then cooled to room temperature, thus producing a two-layer restoration having different shades for the interior and exterior and having an unfinished shape at the base still attached to the mandrel via the sprue.

Further Prophetic Steps

While the milling procedure is occurring, the dentist prepares the patient's tooth, removing carious material and leaving a stump to which the restoration will be attached. A scan is taken of the preparation, digitized, the practitioner marks the margin, and the 3D model of the preparation is meshed with the 3D model of the restoration to determine a new internal surface for milling which is based on the preparation, margin and external shape of the restoration. The internal milling pathway is recalculated to sync with the previous milling pathway but the outer geometry is left as previously milled. In the new CAM milling pathway, the block geometry is calculated based on the shape generated in the previous steps (i.e., the desired inner shape is milled from the two-layer restoration attached to the mandrel).

The unfinished restoration is re-inserted into the mill, the margins and cavity for the preparation are milled, and the finished restoration is removed from the sprue and polished, thus forming a completed restoration ready for cementation to the preparation.

Example 2

Chairside Preparation of an all-Ceramic Biomimetic Dental Restoration for a Patient Needing a Full Crown Using a Cerec 3 milling unit, an external shape in the form of an anterior prep was selected from the software library. Using the same software, an internal cavity was designed to have the same shape as the external surface, but being about 1 mm smaller, thus leaving a 1 mm exterior shell. The design of the outer layer of the restoration was then sent to the milling unit and milled from the dental blank assembly of Preparatory Example 1 to form the outer layer (which includes the desired outer shape and an internal cavity) of the restoration. A sprue was left, attaching the outer layer to the mandrel (thereby forming a "second assembly"). The outer layer and mandrel (i.e., the "second assembly") were removed from the mill.

The cavity formed inside the outer layer was scanned using an E4D system (D4D Technologies, Richardson, Tex.) and the digitized data was treated by the software as an inlay prep to create the design for the internal core having different physical properties from the outer layer. The design for the core was sent to the E4D milling unit and milled from an e.max CAD mill blank, shade HT A2 (Ivoclar Vivadent, Liechtenstein). The milled core was removed from the sprue.

The inside of the outer layer was coated with a slurry of LAVA™ DVS Fusion Porcelain, shade D3 (3M ESPE) and LAVA™ Ceram Modeling Liquid (3M ESPE) and the milled core was pressed into the coated interior. The assembled restoration, i.e., the "second article" still attached to the mandrel via the sprue (i.e., the "third assembly"), was fired in a Vita Vacumat 4000T furnace using the following temperature profile: drying at 403° C. for 6 min., ramped at 30° C./min. to 850° C., held at 850° C. for 10 min., slow cooled to 680° C., then cooled to room temp, thus producing a restoration still attached to the mandrel (i.e., the fired third assembly) and having a lithium disilicate core within a feldspathic porcelain shell.

Further Prophetic Steps

While the milling procedure is occurring, the dentist prepares the patient's tooth, removing carious material and leaving a stump to which the restoration will be attached. A scan is taken of the preparation, digitized, the practitioner marks the margin, and the 3D model of the preparation is meshed with the 3D model of the restoration to determine a new internal surface for milling which is based on the preparation, margin and external shape of the restoration. The internal milling pathway is recalculated to sync with the previous milling pathway but the outer geometry is left as previously milled. In the new CAM milling pathway, the block geometry is calculated based on the shape generated in the previous steps (i.e., the desired inner shape is milled from the two-layer restoration attached to the mandrel).

The unfinished restoration is re-inserted into the mill, margins and cavity for the preparation are milled, the margins and cavity for the preparation are milled, and the finished restoration is removed from the sprue and polished, thus forming a completed restoration.

Preparatory Example 2

Preparation of a Dental Blank Assembly Used in Example 3

Support (Mandrel) Fabrication

A commercially available metal mandrel designed to fit into a Cerec 3 milling unit (Sirona, Germany) was scanned with a LAVA™ ST Scanner (3M ESPE). The scan data were used to mill a LAVA™ Zirconia mill blank (3M ESPE) into the same shape as the metal mandrel, factoring in a shrinkage parameter such that the zirconia mandrel was the proper size after sintering. The milled zirconia was fully sintered per manufacturer's instructions in a LAVA™ Furnace 200 (3M ESPE), thus producing a fully sintered zirconia mandrel.

Mill Blank Attachment to the Mandrel

A lithium disilicate mill blank not having a mandrel (e.max CAD, Ivoclar Vivadent) was placed on a surface and a slurry of LAVA™ Ceram Shoulder Ceramic (3M ESPE) and LAVA™ Ceram Shoulder Liquid (3M ESPE) was liberally painted on both the mill blank and the sintered zirconia mandrel. The mandrel was then pressed onto the blank using finger pressure and the assembly was carefully placed into a furnace (Vita Vacumat 4000T, Vident) and fired with the following temperature profile: 403° C. for 6 min., ramped at 30° C./min. to 850° C. and held there for 1 min. The vacuum was on during the heating and released when the temperature reached 850° C. The fired assembly was slow cooled to 680° C. and then cooled to room temperature, thus producing a mill blank attached to a mandrel (dental blank assembly).

Example 3

Chairside Preparation of an all-Ceramic Dental Restoration for a Patient Needing a Full Crown Using a Cerec 3 milling unit, an external shape in the form of an anterior prep was selected from the software library. Using the same software, an internal cavity was designed to have the same shape as the external surface, but being about 1 mm smaller, thus leaving a 1 mm exterior shell. The design of the outer layer of the restoration was then sent to the milling unit and milled from the dental blank assembly of Preparatory Example 2 to form the outer layer (which includes the desired outer shape and an internal cavity) of the restoration. A sprue was left, attaching the outer layer to the mandrel (thereby forming a "second assembly"). The outer layer and mandrel (i.e., the "second assembly") were removed from the mill.

To fully crystallize the lithium disilicate, the second assembly was placed in a furnace (Vita Vacumat 4000T) and fired with the following temperature profile: 403° C. for 6 min., ramped at 30° C./min. to 850° C. and held there for 10 min. The vacuum was on during the heating and released when the temperature reached 850° C. The fired assembly was slow cooled to 680° C. and then cooled to room temperature, thus producing a fully crystallized milled outer layer of a restoration, still attached to the mandrel (i.e., the fired second assembly).

The hollow interior of the outer layer was then positioned with the open base facing upwards and filled with a slurry of LAVA™ Ceram Overlay Porcelain, shade A2 (3M ESPE) and LAVA™ Ceram Modeling Liquid (3M ESPE). The filled outer layer, still attached to the mandrel, was carefully placed into a Vita Vacumat 4000T furnace and subsequently fired using the following temperature profile: 450° C. for 6 min., ramped at 30° C./min. to 820° C. and held there for 2 min. The vacuum was on during the heating and released when the temperature reached 820° C. The fired assembly (i.e., the fired third assembly) was slow cooled to 600° C. and then cooled to room temperature, thus producing a two-layer restoration having an unfinished shape at the base still attached to the mandrel via the sprue (i.e., a fired third assembly).

Further Prophetic Steps

While the milling procedure is occurring, the dentist prepares the patient's tooth, removing carious material and leaving a stump to which the restoration will be attached. A scan is taken of the preparation, digitized, the practitioner marks the margin, and the 3D model of the preparation is meshed with the 3D model of the restoration to determine a new internal surface for milling which is based on the preparation, margin and external shape of the restoration. The internal milling pathway is recalculated to sync with the previous milling pathway but the outer geometry is left as previously milled. In the new CAM milling pathway, the block geometry is calculated based on the shape generated in the previous steps (i.e., the desired inner shape is milled from the two-layer restoration attached to the mandrel).

The unfinished restoration is re-inserted into the mill, the margins and cavity for the preparation are milled, and the finished restoration is removed from the sprue and polished, thus forming a completed restoration ready for cementation to the preparation.

The embodiments described above and illustrated in the figures are presented by way of example only and are not intended as a limitation upon the concepts and principles of the present disclosure. As such, it will be appreciated by one having ordinary skill in the art that various changes in the workflow steps and their configuration are possible without departing from the spirit and scope of the present disclosure. Various features and aspects of the present disclosure are set forth in the following claims.

What is claimed is:

1. A method of making a multilayer all-ceramic dental appliance, the method comprising:
   providing a first digital surface representation of a desired outer shape of a dental appliance;
   providing a dental blank assembly comprising a blank coupled to a support, the blank being formed of a first material, the first material comprising at least one of a glass, a glass-ceramic, a porcelain, and a ceramic;
   forming a first article of the blank while the blank is coupled to the support, the first article having the desired outer shape based on the first digital surface representation;
   providing a first assembly comprising the first article coupled to the support;
   removing an inner portion of the first article, while the first article is coupled to the support, to form an outer layer of the dental appliance comprising a cavity dimensioned to accommodate an inner layer;
   providing a second assembly comprising the outer layer coupled to the support;
   forming a second article by filling the cavity of the outer layer with a second material adapted to form the inner layer, the second material comprising at least one of a glass, a glass-ceramic, a porcelain, and a ceramic;
   providing a third assembly comprising the second article coupled to the support; and
   firing at least one of the first assembly, the second assembly, and the third assembly.

2. The method of claim 1, wherein the first article, the outer layer, and the second article are each coupled to the support, and wherein firing at least one of the first article, the outer layer and the second article includes firing the support.

3. The method of claim 1, wherein the dental blank assembly is configured to withstand temperatures necessary to fire at least a portion of the assembly in a downstream firing process.

4. The method of claim 1, wherein the dental blank assembly is configured to mechanically withstand a downstream machining process.

5. The method of claim 1, wherein the dental blank assembly further comprises a bonding composition positioned between the blank and the support to couple the blank and the support, the bonding composition having a bonding temperature that is lower than a softening temperature of the blank and that is lower than a softening temperature of the support.

6. The method of claim 5, wherein the support is formed of at least one of a high melting point metal and a ceramic, and wherein a high melting point metal is a metal or metal alloy that has a melting point that is higher than a firing temperature of the blank, and that is higher than the bonding temperature of the bonding composition.

7. The method of claim 6, wherein the blank has a first coefficient of thermal expansion (CTE), wherein the support has a second CTE, and wherein the bonding composition has a third CTE, wherein the first CTE and the second CTE differ by no more than 2.0, wherein the second CTE and the third CTE differ by no more than 2.0, and wherein the first CTE and the third CTE differ by no more than 2.0.

8. The method of claim 1, wherein the dental blank assembly further comprises a means for coupling the blank and the support, wherein the means for coupling includes at least one of a mechanical inter-engagement, a direct bond, a bonding composition, and a combination thereof.

9. The method of claim 1, wherein the support is formed of at least one of a metal, metal alloy, and a ceramic.

10. The method of claim 1, wherein the dental blank assembly is formed of a unitary construction, such that the blank and the support are integrally formed of the same material.

11. The method of claim 1, further comprising:
providing a dental object having an outer shape comprising the negative of a desired inner shape of the dental appliance;
acquiring a second digital surface representation of the outer shape of the dental object;
subtractively forming the desired inner shape in the second article based on the second digital surface representation to form the dental appliance having the desired inner shape and the desired outer shape.

12. The method of claim 11, wherein the dental object includes at least one of a tooth stump, an implant, an implant abutment, a healing cap, and a combination thereof.

13. The method of claim 11, wherein acquiring a second digital surface representation of the outer shape of the dental object includes optically scanning the dental object.

14. The method of claim 11, wherein subtractively forming the desired inner shape in the second article includes milling the desired inner shape.

15. The method of claim 11, wherein at least two of forming a first article, removing an inner portion of the first article, and subtractively forming the desired inner shape in the second article are performed by the same fabrication tool.

16. The method of claim 11, wherein at least two of forming a first article, removing an inner portion of the first article, and subtractively forming the desired inner shape in the second article occur at different locations from one another.

17. The method of claim 11, wherein at least one of providing a dental object and acquiring a second digital surface representation occurs during or after at least one of forming a first article, removing an inner portion of the first article, and forming a second article, and wherein subtractively forming the desired inner shape occurs separately from and subsequently to forming a first article of a first material having the desired outer shape.

18. The method of claim 1, further comprising repeating the removing an inner portion of the first article step and the forming a second article step as many times as desired to form a second article having a desired number of layers and comprising the inner layer.

19. The method of claim 1, wherein the second material has at least one material property that is different from the first material, such that the dental appliance is biomimetic.

20. The method of claim 1, wherein the second material has at least one optical property that is different from the first material, such that the dental appliance is multi-chromatic.

* * * * *

UNITED STATES PATENT AND TRADEMARK OFFICE
CERTIFICATE OF CORRECTION

PATENT NO. : 8,844,139 B2
APPLICATION NO. : 13/995553
DATED : September 30, 2014
INVENTOR(S) : Ryan Johnson et al.

It is certified that error appears in the above-identified patent and that said Letters Patent is hereby corrected as shown below:

On the title page in the print figure reference numeral 614 line 2 delete "resoration" and insert -- restoration --, therefor. Reference numeral 617 line 2 delete "thefirst" and insert -- the first --, therefor

IN THE DRAWINGS

Sheet 3 of 3 (Reference Numeral 614) Fig. 6
Line 2, Delete "resoration" and insert -- restoration --, therefor.

Sheet 3 of 3 (Reference Numeral 617) Fig. 6
Line 2, Delete "thefirst" and insert -- the first --, therefor.

IN THE SPECIFICATION

Column 7
Line 16-17, Delete "Germany)" and insert -- Germany). --, therefor.

Column 20
Line 20-21, Delete "VM7(VM9" and insert -- VM7/VM9 --, therefor.

Column 27
Line 16, Delete "includes" and insert -- include --, therefor.

Column 30
Line 14, Delete "a" and insert -- as --, therefor.

Signed and Sealed this
Tenth Day of March, 2015

Michelle K. Lee
*Deputy Director of the United States Patent and Trademark Office*

Column 31
Line 45, Delete "handling" and insert -- handling. --, therefor.
Line 45, Delete "As further...composition 108." and insert the same on Col. 31, line 46 as a new paragraph.

Column 40
Line 47, Delete "shock-aborptive," and insert -- shock-absorptive, --, therefor.